United States Patent [19]

Chakravarty et al.

[11] Patent Number: 5,204,354

[45] Date of Patent: Apr. 20, 1993

[54] SUBSTITUTED QUINAZOLINONES AS NEUROTENSIN ANTAGONISTS USEFUL IN THE TREATMENT OF CNS DISORDERS

[75] Inventors: Prasun K. Chakravarty, Edison; E. M. Naylor, Scotch Plains, both of N.J.; Richard W. Ransom, New Britain, Pa.

[73] Assignee: Merck & Co., Inc., Rahway, N.J.

[21] Appl. No.: 826,726

[22] Filed: Feb. 14, 1992

[51] Int. Cl.$^5$ ............... C07D 239/91; A61K 31/505
[52] U.S. Cl. ............... 514/259; 514/258; 514/260; 514/270; 544/283; 544/284; 544/287
[58] Field of Search ............ 514/259, 260, 258, 270; 544/283, 284, 287

[56] References Cited

U.S. PATENT DOCUMENTS

| | | | |
|---|---|---|---|
| 4,425,269 | 1/1984 | Christy et al. | 260/112.5 R |
| 4,439,359 | 3/1984 | Holly et al. | 260/112.5 R |
| 5,064,825 | 11/1991 | Chakravarty et al. | 514/221 |
| 5,075,313 | 12/1991 | Yu et al. | 514/259 |
| 5,102,880 | 4/1992 | Chakravarty et al. | 514/212 |
| 5,128,335 | 7/1992 | Guthikonda et al. | 514/210 |
| 5,130,306 | 7/1992 | Duggan et al. | 514/121 |

FOREIGN PATENT DOCUMENTS

| | | | |
|---|---|---|---|
| 0367944 | 5/1990 | European Pat. Off. | 544/282 |
| 0411766 | 2/1991 | European Pat. Off. | 514/259 |
| 0477049A1 | 8/1991 | France | 514/221 |

OTHER PUBLICATIONS

G. A. Cain, et al. Neurotensin Based Analgesics: 203rd National Meeting of the Am. Chem. Soc. Apr. 5-10, (1992).

*Primary Examiner*—Floyd D. Higel
*Attorney, Agent, or Firm*—Valerie J. Camara; William H. Nicholson; Joseph F. DiPrima

[57] ABSTRACT

Substituted quinazolinones of the formula are useful as neurotensin antagonists.

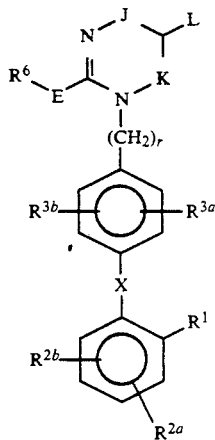

14 Claims, No Drawings

1

SUBSTITUTED QUINAZOLINONES AS NEUROTENSIN ANTAGONISTS USEFUL IN THE TREATMENT OF CNS DISORDERS

INTRODUCTION OF THE INVENTION

This invention is concerned with a method of treating disease states mediated by neurotensin by the administration to a patient in need of treatment of a therapeutically effective amount of a neurotensin antagonist which is a substituted quinazolinone of structure formula I:

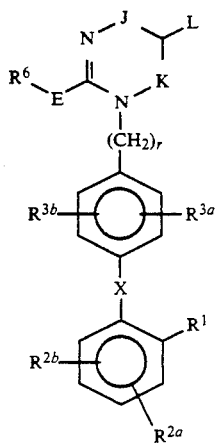
(I)

which depending on the definition of J and K gives rise to two embodiments Ia and Ib within the genus:

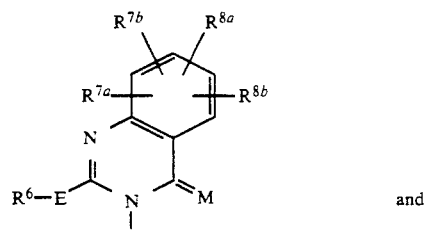
Ia and

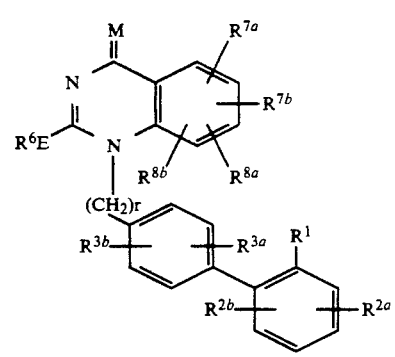
Ib wherein M is =O or =NR$^{22}$.

As neurotensin antagonists these compounds find utility in the treatment of CNS dysfunctions such as psychoses, depression, cognitive dysfunction, such as Alzheimer's disease, anxiety, tardive dyskinesia, drug dependency, panic attack and mania. The neurotensin antagonist property also imparts to the compounds utility in GI disorders such as gastroesophageal reflux disorder (GERD), irritable bowel syndrome, diarrhea, cholic, ulcer, GI tumors, dyspepsia, pancreatitis, esophagitis and gastroparesis. The known ability of neurotensin to release mast cell histamine indicates that antagonists will be useful in the treatment of allergic and inflammatory conditions.

BACKGROUND OF THE INVENTION

Neurotensin (NT) is a tridecapeptide hormone (pGlu-Leu-Tyr-Glu-Asn-Lys-Pro-Arg-Arg-Pro-Tyr-Ile-Leu-OH), originally isolated from the bovine hypothalamus [Carraway, R. and Leeman, S. E., J. Biol. Chem.,248, 6854 (1973)], has subsequently been shown to be distributed in the brain [Uhl, G. R., et al., Proc. Natl. Acad. Sci. USA, 74, 4059–4063 (1977)], gastrointestinal tract [1) Kitabgi, P., Carraway, R. and Leeman, S. E., J. Biol. Chem., 251, 7053 (1976); 2) Carraway, R., Kitabgi, P., and Leeman, S. E., J. Biol. Chem., 253, 7996 (1978); 3) Helmstadler, V., Taugner, C., Feurle, G. E. and Frossman, W.G., Histochemistry, 53, 35–41 (1977)] and pancreas [Feurle, G.E. and Niestroj, S., Pancreas, 6, 202–207 (1991) and references cited therein] of various animals including human [Mai, J. K., et al., Neuroscience, 22, 499–524 (1987)]. Although the physiological role of neurotensin has not yet been clearly understood, this endogenous peptide participates in a wide spectrum of central [1). Prange, A.J. and Nemeroff, C.B., Annal. NY Acad. Sciences, 400, 368-375 (1982); 2). Stowe, Z. N. and Nemeroff, C. B., Life Sci., 49, 987–1002, (1991); 3) Kitabgi, P., Neurochem. Int., 14, 111–119 (1989); 4) Levant and Nemeroff, C. B., Current topics in Neuroendocrinology, 8, 231–262 (1988)] and peripheral [Leeman, S. E., Aronin, N. and Ferris, C., Hormone Res., 38, 93–132 (1982)] biological functions.

Neurotensin is also known to release mast cell histamine, indicating that antagonists will be useful in the treatment of allergic and inflammatory conditions, as well. [See, Rossei, S. S. and Miller, R. J., Life Sci., 31, 509–516 (1982) and Kurose, M. and Saeki, K., Eur. J. Pharmacol., 76, 129-136 (1981).]

Neurotensin, like most other peptides, is unable to cross the blood-brain barrier (BBB). However, certain peripheral effects of neurotensin have been observed after central administration of the peptide [Prange, A. J. and Nemeroff, C. B., Annal. NY Acad. Sciences, 400, 368–391 (1982)]. The direct application of neurotensin into the brain causes hypothermia, potentiation of barbiturate induced sedation, catalepsy, antinociception, blockade of psychostimulant-induced locomotor activity and reduced food consumption. In the central nervous system (CNS), neurotensin behaves as a neurotransmitter or neuromodulator [1) Uhl, G. R. and Snyder, S. H., Eur. J. Pharmacol., 41, 89–91 (1977); 2) Uhl, G. R., Annal. NY Acad. Sciences, 400, 132–149 (1982)], and has been shown to have close anatomical and biochemical associations with the dopaminergic (DA) system [Nemeroff, C. B., et al. Annal. NY Acad. Sciences, 400, 330–344 (1982)]. Neurotensin increases the synthesis and the turnover of DA in rat brain. Acute and chronic treatment with clinically efficacious antipsychotic drugs (e.g., haloperidol, chlorpromazine) have consistently demonstrated an increase in neurotensin concentrations in the nucleus accumbens and striatum while phenothiazines that are not antipsychotics did not produce this increase. Behaviorally, neurotensin, after central administration, mimics the effects of systemically administered neuroleptics. However, unlike classical neuroleptics (which primarily acts on D2 receptors), neurotensin fails to bind to dopamine receptors or inhibit cAMP accumulation following DA receptor activation. Neurotensin does not block the stereotypy induced by DA agonists. The post-mortem studies of patients with schizophrenia showed an increase in the level of neurotensin in the Brodman's area 32 of human brain [Nemeroff, C. B., et. al., Science., 221, 972-975 (1983) and references cited therein], which suggest possible roles of neurotensin in the pathophysiology of this disease. Neurotensin receptors have also been implicated in Parkinson's disease and progressive supranuclear palsy [Chinaglia, G. et al., Neuroscience, 39, 351-360 (1990)].

Of the total body neurotensin in many mammalian species, more than 80% is present in the gastrointestinal tract, especially in the distal small intestine in the endocrine like N-cells. In the gut, neurotensin stimulates pancreatic secretion [Sakamoto, T., et al, Surgery, 96, 146-53 (1984)], inhibits gastric acid secretion and gastric emptying [Blackburn, A. M., Lancet, 1, 987-989 (1980)]. Neurotensin also stimulates the growth of small intestinal mucosa in an isolated defunctional loop of jejunum, which suggests a direct systemic effect of neurotensin in the gut. In addition, neurotensin can stimulate pancreatic exocrine secretion in mammals [Iwatsuki, K., et al., Clin. Expt. Pharmacol. Physiol., 18, 475-481 (1991) and references cited therein].

From the structural work, it is evident that the biological activity of neurotensin resides within the carboxy terminal five or six amino acid residues. The C-terminal hexapeptide NT$^{8-13}$ has displayed full biological activity of the tridecapeptide. In contrast, all amino terminal partial sequences are essentially inactive [Leeman, S. E. and Carraway, R. E., Annal. NY Acad. Sciences, 400, 1-16 (1982)]. The C-terminal COOH group and two Arg residues are essential for the biological activity of NT$^{8-13}$ as well as neurotensin. L-amino acids are required at positions-9,10,11 and 13, and only Arg$^8$ can be replaced by D-Arg without loss of any activity. At the position-11, an aromatic amino acid is essential. Similarly, alkyl side-chains of Ile$^{12}$ and Leu$^{13}$ are also necessary for full biological activity [Kitabgi, P., Annal. NY Acad. Sciences, 400, 37-53 (1982)]. Most of the analogues of neurotensin examined generally behaved as agonists. However, two analogues D-Trp$^{11}$-NT and Tyr(Me)$^{11}$-NT have displayed partial antagonist activity [Rioux, F. R., et al., Eur. J. Pharmacol., 66, 373-379 (1980)].

The compounds useful in the novel method of treatment of this invention are known in the art having been published in European Patent Application EP 411,766 (Merck & Co., Inc.) where they are alleged to be angiotensin-II (A-II) receptor antagonists useful in the treatment of hypertension, ocular hypertension.

Although there are reports of peptidic neurotensin antagonists, they are unstable and not orally active and none are clinically available. There are no reports of non-peptidic neurotensin antagonists.

Now with this invention, there are provided non-peptidic neurotensin antagonists.

DETAILED DESCRIPTION OF THE INVENTION

The compounds useful in the novel method of treatment of this invention have structural formula I:

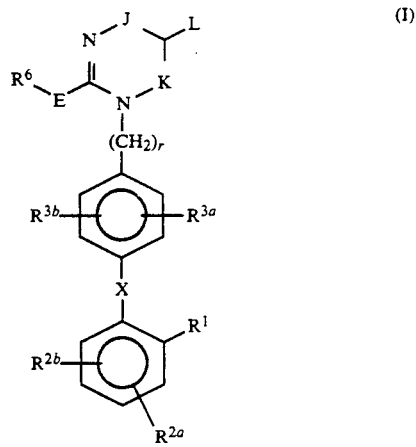

or a pharmaceutically acceptable salt thereof, wherein:

L is connected with J or K to form an aromatic ring as defined below;

J is —C(=M)— or J and L are connected together to form a 6 carbon aromatic ring substituted with $R^{7a}$, $R^{7b}$, $R^{8a}$ and $R^{8b}$, provided that only one of J and K is —C(=M)—;

K is —C(=M)— or K and L are connected together to form a 6 carbon aromatic ring substituted with $R^{7a}$, $R^{7b}$, $R^{8a}$ and $R^{8b}$, provided that only one of J and K is —C(=M)—;

M is O or $NR^{22}$;

$R^1$ is:
(a) —NHSO$_2$R$^{23}$,
(b) —NHSO$_2$NHCOR$^{23}$,
(c) —NHCONHSO$_2$R$^{23}$,
(d) —SO$_2$NHR$^{23}$,
(e) —SO$_2$NHCOR$^{23}$,
(f) —SO$_2$NHCONR$^4$R$^{23}$,
(g) —SO$_2$NHCOOR$^{23}$,
(h) —SO$_2$NHOR$^{23}$,
(i) —CH$_2$SO$_2$NHCOR$^{23}$,
(j) —CH$_2$SO$_2$NHCONHR$^{23}$,
(k) —CO$_2$H, or
(l) —1H-tetrazol-5-yl;

$R^{2a}$ and $R^{2b}$ are each independently
(a) H,
(b) Cl, Br, I, F,
(c) CF$_3$,
(d) C$_1$-C$_6$-alkyl,
(e) C$_1$-C$_6$-alkoxy,
(f) C$_1$-C$_6$-alkyl-S—,
(g) C$_2$-C$_6$-alkenyl,
(h) C$_2$-C$_6$-alkynyl,
(i) C$_3$-C$_7$-cycloalkyl,
(j) aryl, or
(k) aryl-C$_1$-C$_6$-alkyl;

$R^{3a}$ is
(a) H,
(b) Cl, Br, I, F,
(c) C$_1$-C$_6$-alkyl,
(d) C$_1$-C$_6$-alkoxy, or
(e) C$_1$-C$_6$-alkoxyalkyl;

$R^{3b}$ is
(a) H,
(b) Cl, Br, I, F,
(c) $C_1-C_6$-alkyl,
(d) $C_3-C_7$-cycloalkyl,
(e) $C_1-C_6$-alkoxy,
(f) $CF_3$,
(g) $C_2-C_6$-alkenyl, or
(h) $C_2-C_6$-alkynyl;

$R^4$ is
(a) H,
(b) $C_1-C_6$-alkyl,
(c) aryl, wherein aryl is phenyl or naphthyl, either unsubstituted or substituted with one or two substituents selected from the group consisting of halogen, $N(R^4)_2$, $CO_2R^4$, $C_1-C_4$-alkyl, $C_1-C_4$-alkoxy, $NO_2$, $CF_3$, $C_1-C_4$-alkylthio, and OH;
(d) aryl-$C_1-C_6$ alkyl, or
(e) heteroaryl, wherein heteroaryl is an unsubstituted, monosubstituted or disubstituted five or six membered aromatic ring such as thiazole, imidazole, pyrazole, oxazole, pyridine, thiazine, pyrazine, pyrimidine or the like which contains from 1 to 3 heteroatoms selected from the group consisting of O, N and S and wherein the substituents are members selected from the group consisting of —OH, —SH, —$C_1-C_4$-alkyl, —$C_1-C_4$-alkoxy, —$CF_3$, Cl, Br, F, I, —$NO_2$, —$CO_2H$, —$CO_2$—($C_1-C_4$-alkyl), —$NH_2$, —$NH(C_1-C_4$-alkyl) and —$N(C_1-C_4$-alkyl)$_2$;

E is a single bond, —$NR^{13}(CH_2)_s$—, —$S(O)_x(CH_2)_s$— where x is 0 to 2 and s is 0 to 5, —CH(OH)—, —O—, or —CO—;

$R^6$ is
(a) H,
(b) aryl,
(c) $C_1-C_6$-alkyl, $C_2-C_5$-alkenyl or $C_2-C_5$-alkynyl each of which can be unsubstituted or substituted with a substituent selected from the group consisting of aryl, Cl Br, I, F, $C_3-C_7$-cycloalkyl, —$NH_2$, —$NH(C_1-C_4$-alkyl), —$OR^4$, —$N(C_1-C_4$-alkyl)$_2$, —NH—$SO_2R^4$, —$COOR^4$, and —$SO_2NHR^9$; or
(d) heteroaryl, or
(e) $C_3-C_7$-cycloalkyl;

$R^{7a}$ and $R^{7b}$ are independently
(a) H,
(b) $C_1-C_6$-alkyl, $C_2-C_6$-alkenyl or $C_2-C_6$-alkynyl,
(c) Cl, Br, I, F,
(d) $CF_3$,
(e) when $R^{7a}$ and $R^{7b}$ are bonded to adjacent carbon atoms, they can be joined to form a phenyl ring, or
(f) aryl;

$R^{8a}$ and $R^{8b}$ are independently
(a) H,
(b) $C_1-C_6$-alkyl, unsubstituted or substituted with a substituent selected from the group consisting of —OH, -guanidino, $C_1-C_4$-alkoxy, —$N(R^4)_2$, $COOR^4$, —$CON(R^4)_2$, —O—$COR^4$, -aryl, -heteroaryl, —$S(O)_x$—$R^{23}$, -tetrazol-5-yl, —$CONHSO_2R^{23}$, —$SO_2NH$-heteroaryl, —$SO_2NHCOR^{23}$, —$PO(OR^4)_2$, —$PO(OR^4)R^9$, —$SO_2NH$—CN, —$NR^{10}COOR^{23}$, morpholino, N—($C_1-C_6$-alkyl)piperazine, and —$COR^4$,
(c) —CO-aryl,
(d) —$C_3-C_7$-cycloalkyl,
(e) Cl, Br, I, F,
(f) —OH,
(g) —$OR^{23}$,
(h) —$C_1-C_4$-perfluoroalkyl,
(i) —$S(O)_x$—$R^{23}$,
(j) —$COOR^4$,
(k) —$SO_3H$,
(l) —$NR^4R^{23}$,
(m) —$NR^4COR^{23}$,
(n) —$NR^4COOR^{23}$,
(o) —$SO_2NR^9R^{10}$,
(p) —$NO_2$,
(q) —$NR^4SO_2R^{23}$,
(r) —$NR^4CONR^4R^{23}$, (s) 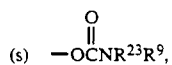

(t) -aryl or -heteroaryl as defined above,
(u) —$NHSO_2CF_3$,
(v) —$SO_2NH$-heteroaryl,
(w) —$SO_2NHCOR^{23}$,
(x) —$CONHSO_2R^{23}$,
(y) —$PO(OR^4)_2$,
(z) —$PO(OR^4)R^9$,
(aa) —tetrazol-5-yl,
(bb) —CONH(tetrazol-5-yl),
(cc) —$COR^4$,
(dd) —$SO_2NHCN$ (ee) 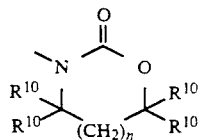

where n = 0 or 1, (ff) —CO-heteroaryl,
(gg) —$NR^4SO_2NR^{23}R^9$,
(hh) —N[$CH_2CH_2$]$_2NR^{24}$, wherein $R^{24}$ is $C_1-C_6$-alkyl, $C_3-C_7$-cycloalkyl, $CONR^9R^{10}$, heteroaryl, such as pyridyl, phenyl —CO—$C_3-C_7$-cycloalkyl, or
(ii) —N[$CH_2CH_2$]$_2O$;

$R^9$ is H, $C_1-C_5$-alkyl, aryl or arylmethyl;
$R^{10}$ is H, $C_1-C_4$-alkyl;
$R^{11}$ is H, $C_1-C_6$-alkyl, $C_1-C_4$-alkenyl, $C_1-C_4$-alkoxy alkyl, or

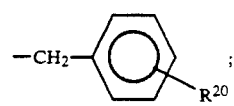

$R^{12}$ is —CN, —$NO_2$, —$CF_3$ or —$CO_2R^4$;
$R^{13}$ is H, ($C_1-C_4$-alkyl)CO—, $C_1-C_6$-alkyl, allyl, $C_3-C_6$-cycloalkyl, aryl or arylmethyl;
$R^{14}$ is H, $C_1-C_8$-alkyl, $C_1-C_8$-perfluoroalkyl, $C_3-C_6$-cycloalkyl, aryl or arylmethyl;
$R^{15}$ is H, $C_1-C_6$-alkyl;
$R^{16}$ is H, $C_1-C_6$-alkyl, $C_3-C_6$-cycloalkyl, aryl or arylmethyl;
$R^{17}$ is —$NR^9R^{10}$, —$OR^{10}$, —$NHCONH_2$, —$NHCSNH_2$,

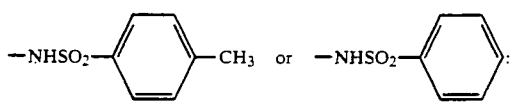 or 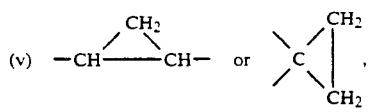

$R^{18}$ and $R^{19}$ are independently $C_1$-$C_4$-alkyl or taken together are —$(CH_2)_q$— where q is 2 or 3;

$R^{20}$ is H, —$NO_2$, —$NH_2$, —OH or —$OCH_3$;

$R^{21}$ is H, aryl, or $C_1$-$C_4$-alkyl optionally substituted with aryl, —$NH_2$, —$NH(C_1$-$C_4$-alkyl), —$N(C_1$-$C_4$-alkyl)$_2$, —$CO_2R^4$, —OH, —$SO_3H$, or —$SO_2NH_2$;

$R^{22}$ is
- (a) aryl,
- (b) heteroaryl,
- (c) $C_1$-$C_6$-alkyl unsubstituted substituted with a substituent selected from the group consisting of aryl, heteroaryl, —OH, —$NH_2$, —$NH(C_1$-$C_4$-alkyl), —$N(C_1$-$C_4$-alkyl)$_2$, —$CO_2R^4$, Cl, Br, F, I, and —$CF_3$, or
- (d) perfluoro-$C_1$-$C_4$-alkyl;

$R^{23}$ is
- (a) aryl,
- (b) heteroaryl,
- (c) $C_3$-$C_7$-cycloalkyl,
- (d) $C_1$-$C_8$-alkyl wherein alkyl is unsubstituted or substituted with one or two substituents selected from the group consisting of aryl, heteroaryl, —OH, —SH, $C_1$-$C_4$-alkyl, —$O(C_1$-$C_4$-alkyl), —$S(C_1$-$C_4$-alkyl), —$CF_3$, Cl, Br, F, I, —$NO_2$, —$CO_2H$, —$CO_2$-$C_1$-$C_4$-alkyl, —$NH_2$, —$NR^4CO_2R^{22}$, —$NH(C_1$-$C_4$-alkyl), —$N(C_1$-$C_4$-alkyl)$_2$, —$PO_3H_2$, —$PO(OH)(O$—$C_1$-$C_4$-alkyl), —$PO(OR^4)R^9$, —$NR^4COR^{22}$, —$CONR^4R^{22}$, —$O$-$CONR^4R^{22}$, —$SO_2NR^4R^{22}$, —$NR^4SO_2R^{22}$, or
- (e) perfluoro-$C_1$-$C_4$-alkyl;

X is
- (a) a carbon-carbon single bond,
- (b) —CO—,
- (c) —O—,
- (d) —S—,
- (e) —N—, $R^{13}$
- (f) —CON—, $R^{15}$
- (g) —NCO—, $R^{15}$
- (h) —$OCH_2$—,
- (i) —$CH_2O$—
- (j) —$SCH_2$—,
- (k) —$CH_2S$—,
- (l) —$NHC(R^9)(R^{10})$,
- (m) —$NR^9SO_2$—,
- (n) —$SO_2NR^9$—,
- (o) —$C(R^9)(R^{10})NH$—,
- (p) —CH=CH—,
- (q) —CF=CF—,
- (r) —CH=CF—,
- (s) —CF=CH—,
- (t) —$CH_2CH_2$—,
- (u) —$CF_2CF_2$—,
- (v) —CH$\underset{CH_2}{\diagup\diagdown}$CH— or $\underset{CH_2}{\diagup\diagdown}$C$\underset{CH_2}{\diagdown\diagup}$,
- (w) —CH—, $OR^{14}$
- (x) —CH—, $OCOR^{16}$
- (y) —C—, $NR^{17}$ or
- (z) —C—; $R^{18}O$ $OR^{19}$ r is 1 or 2.

The terms "alkyl", "alkenyl", "alkynyl": and the like include both the straight chain and branched chain species of these generic terms wherein the number of carbon atoms in the species permit. Unless otherwise noted, the specific names for these generic terms shall means the straight chain species. For example, the term "butyl" shall mean the normal butyl substituent, n-butyl.

One embodiment of the compounds of formula (I) are those compounds wherein:

J is —C(=O)— or —C(=$NR^{22}$),

K and L are connected together to form a 6 carbon aromatic ring substituted with $R^{7a}$, $R^{7b}$, $R^{8a}$ and $R^{8b}$.

A class of compounds within this embodiment is that wherein:

$R^1$ is:
- (a) —$NHSO_2R^{23}$,
- (b) —$NHSO_2NHCOR^{23}$,
- (c) —$NHCONHSO_2R^{23}$,
- (d) —$SO_2NHR^{23}$,
- (e) —$SO_2NHCOR^{23}$,
- (f) —$SO_2NHCONR^4R^{23}$,
- (g) —$SO_2NHCOOR^{23}$,
- (h) —$SO_2NHOR^{23}$,
- (i) —$CH_2SO_2NHCOR^{23}$,
- (j) —$CH_2SO_2NHCONHR^{23}$,
- (k) —$CO_2H$, or
- (l) —1H-tetrazol-5-yl;

$R^{2a}$ is H;

$R^{2b}$ is H, F, Cl, $CF_3$, $C_1$-$C_6$-alkyl, $C_2$-$C_4$-alkenyl, or $C_2$-$C_4$-alkynyl, aryl or aryl-$C_1$-$C_6$-alkyl $R^{3a}$ is H;

$R^{3b}$ is H, F, Cl, $CF_3$, $C_1$-$C_4$-alkyl, $C_2$-$C_4$-alkenyl, $C_2$-$C_4$-alkynyl, or $C_5$-$C_6$-cycloalkyl, E is a single bond, —O—, —S—, or —$SO_2$—;

$R^6$ is
- (a) $C_1$-$C_5$-alkyl either unsubstituted or substituted with a substituent selected from the group consisting of $C_3$-$C_5$-cycloalkyl, Cl, —O—$CH_3$, —$OC_2H_5$, or F,
- (b) $C_2$-$C_5$-alkenyl or $C_2$-$C_5$-alkynyl,
- (c) $C_3$-$C_5$-cycloalkyl, or
- (d) aryl;

$R^{7a}$ and $R^{7b}$ are independently
- (a) H,
- (b) $C_1$-$C_6$-alkyl, or
- (c) aryl;

$R^{8a}$ and $R^{8b}$ are independently
(a) H,
(b) $C_1$-$C_6$-alkyl unsubstituted or substituted with COOR$^4$, OCOR$^{4a}$, OH, or aryl,
(c) —OH,
(d) —NO$_2$,
(e) —NHCOR$^{23}$,
(f) —$C_1$-$C_4$-alkoxy,
(g) —NHCO$_2$R$_{23}$,
(h) —NR$^4$R$^{23}$,
(i) —Cl, F, Br,
(j) —CF$_3$,
(k) —CO$_2$R$^4$,
(l) —CO-aryl,
(m) —S(O)$_x$—$C_1$-$C_4$-alkyl,
(n) —SO$_2$—NH—$C_1$-$C_4$-alkyl,
(o) —SO$_2$—NH-aryl,
(p) —NHSO$_2$CH$_3$,
(q) -aryl,
(r) —NHCONR$^4$R$^{23}$,
(s) —N[CH$_2$CH$_2$]$_2$NR$^{24}$, or
(t) —N[CH$_2$CH]$_2$O;
X is a single bond;
r is one.

Another class of this embodiment are those compounds of Formula (I) wherein:
R$^1$ is:
(a) —NHSO$_2$R$^{23}$,
(b) —NHSO$_2$NHCOR$^{23}$,
(c) —NHCONHSO$_2$R$^{23}$,
(d) —SO$_2$NHR$^{23}$,
(e) —SO$_2$NHCOR$^{23}$,
(f) —SO$_2$NHCONR$^4$R$^{23}$,
(g) —SO$_2$NHCOOR$^{23}$,
(h) —SO$_2$NHOR$^{23}$,
(i) —CH$_2$SO$_2$NHCOR$^{23}$,
(j) —CH$_2$SO$_2$NHCONHR$^{23}$,
(k) —1H-tetrazol-5-yl, or
(l) —CO$_2$H;
E is a single bond;
r is one;
R$^6$ is —$C_1$-$C_4$-alkyl, -cyclopropyl, —CH$_2$CH$_2$CH$_2$CF$_3$, —CH$_2$CH$_2$CF$_3$, -$C_2$-$C_5$-alkenyl, or -cyclopropylmethyl; and
R$^{8a}$ and R$^{8b}$ are each independently H, —$C_1$-$C_4$-alkyl, -aryl, —NO$_2$, —NR$^4$R$^{23}$, —NHCOOR$^{23}$, —Cl, —CH$_2$COOH, —S(O)$_x$-$C_1$-$C_4$-alkyl, NHCONR$^4$R$^{23}$, NHCOR$^{23}$, CO$_2$R$^4$, —F, N[CH$_2$CH$_2$]$_2$NR$^{24}$, or N[CH$_2$CH$_2$]$_2$O.

Another class of this embodiment are those compounds of Formula (I) wherein:
R$^1$ is
(a) —CH$_2$SO$_2$NHCOR$^{23}$,
(b) —1H-tetrazol-5-yl,
(c) —SO$_2$NHCOR$^{23}$,
(d) —SO$_2$NHCONR$^4$R$^{23}$,
(e) —SO$_2$NHCOOR$^{23}$, or
(f) —SO$_2$NHOR$^{23}$;
R$^6$ is -n-propyl, ethyl, iso-propyl, -n-butyl, -trans-2-butenyl, -cyclopropyl, or -cyclopropylmethyl;
R$^{8a}$ and R$^{8b}$ are each independently H, —NO$_2$, —C$_1$-$C_4$-alkyl, -aryl, —NHCOCH$_3$, —S(O)$_x$—($C_1$-$C_4$-alkyl), —N(CH$_3$)$_2$, —NHCOCH$_2$NH$_2$, —COOH, —COOCH$_3$, —CH$_2$OCOCH$_3$, —CH$_2$COOCH$_3$, —NHCON(R$^4$)$_2$, —NHCO$_2$R$^4$, —CH$_2$COOH, CH$_2$OH, NHMe, N[CH$_2$CH$_2$]$_2$NR$^{24}$, or N[CH$_2$CH$_2$]$_2$O.

Also exemplifying this class are the compounds indicated in the Table I below:

TABLE I

| R$^1$ | R$^6$ | R$^{8a}$ |
|---|---|---|
| 1H-tetrazol-5-yl | cyclopropyl | N(pentyl)(benzoyl) |
| 1H-tetrazol-5-yl | cylcopropyl | N(benzyl)(benzoyl). |

In a second embodiment of the novel compounds of this invention are those compounds of formula (I) wherein:
K is —C(O)— or —C(=NR$^{22}$); and
J and L are connected together to form a 6 carbon aromatic ring substituted with R$^{7a}$, R$^{7b}$, R$^{8a}$ and R$^{8b}$; and, the class and sub-class of this embodiment are as defined above.

Further exemplifying this class are the compounds indicated in Tables II and III below:

TABLE II

| R$^6$ | R$^{7a}$ | R$^{8a}$ | R$^{23}$ |
|---|---|---|---|
| n-butyl | H | —N[CH$_2$CH$_2$]$_2$N-pyrid-2-yl | -cyclopropyl |
| isopropyl | CH$_3$ | —H | —CH$_2$CH$_2$CH(NHBoc)CO$_2$t-butyl |

TABLE II-continued

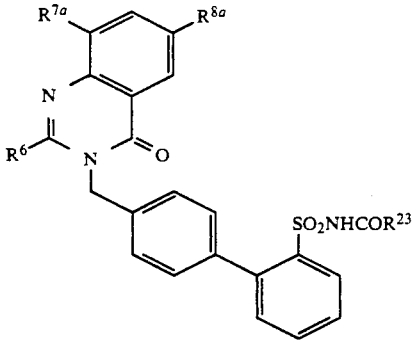

| R⁶ | R⁷ᵃ | R⁸ᵃ | R²³ |
|---|---|---|---|
| isopropyl | CH₃ | —H | —CH₂CH₂CH(NH₂)CO₂H |
| isopropyl | CH₃ | —H | —(CH₂)₅N(CH₃)₂ |
| butyl | H | —N[CH₂CH₂]₂NCOCH₃ | -cyclopropyl |
| propyl | H | —CH₃ | -cyclopropyl |
| butyl | CH₃ | —H | —(CH₂)₅NHBoc |
| butyl | CH₃ | —H | —(CH₂)₅NH₂ |
| butyl | H | -isopropyl | —CH₂CH₂-cyclopentyl |
| propyl | H | —N(CH₃)CO₂isobutyl | -phenyl |
| butyl | H | -isopropyl | —(CH₂)₅NHBoc |
| butyl | H | -isopropyl | —(CH₂)₅NH₂ |
| butyl | H | —N[CH₂CH₂]₂N-cyclopropyl | -cyclopropyl |
| propyl | H | -isopropyl | —(CH₂)₄CO₂CH₃ |
| propyl | H | —N(CH₃)CO₂-isobutyl | -cyclopropyl |
| ethyl | H | —N(benzyl)(benzoyl) | -phenyl |
| propyl | H | -isopropyl | —(CH₂)₄CO₂H |
| propyl | H | —N(pentyl)(benzoyl) | -cyclopropyl |
| propyl | H | —N(benzyl)CO₂-n-butyl | -cyclopropyl |
| propyl | H | —N(benzyl)CO₂-n-butyl | —CH₂NHBoc |
| propyl | H | —N(propyl)(acetyl) | -cyclopropyl |
| propyl | H | —N(pentyl)CO-cyclopropyl | -cyclopropyl |
| propyl | H | —N[CH₂CH₂]₂N-pyrid-2-yl | -cyclopropyl |
| propyl | H | -isopropyl | -cyclopropyl |

TABLE III

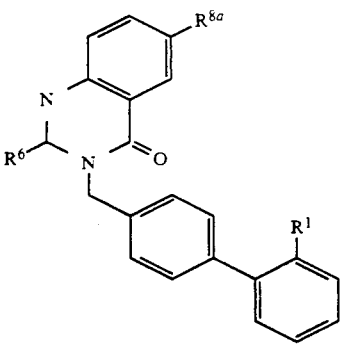

| R¹ | R⁶ | R⁸ᵃ |
|---|---|---|
| 1H-tetrazol-5-yl | n-propyl | —N(pentyl)(benzyl) |
| 1H-tetrazol-5-yl | methyl | —N(benzyl)CO₂-isobutyl |
| 1H-tetrazol-5-yl | n-butyl | —N(benzyl)CO₂-n-propyl |
| 1H-tetrazol-5-yl | n-propyl | —N(pentyl)CObenzyl |
| 1H-tetrazol-5-yl | n-propyl | —N(cyclohexyl)CO₂-n-propyl |
| 1H-tetrazol-5-yl | n-propyl | —N(benzyl)CO₂—CH₂CH₂OCH₃ |
| 1H-tetrazol-5-yl | n-propyl | —N(n-pentyl)(benzoyl) |
| 1H-tetrazol-5-yl | n-propyl | —N(benzyl)CO₂-t-butyl |
| 1H-tetrazol-5-yl | n-propyl | —N(benzyl)(SO₂-butyl) |
| 1H-tetrazol-5-yl | n-propyl | —N(n-pentyl)(4-chlorobenzoyl) |
| 1H-tetrazol-5-yl | n-propyl | —N(benzyl)CON(CH₃)(propyl) |
| 1H-tetrazol-5-yl | n-butyl | —N(benzyl)CON(CH₃)(propyl) |
| 1H-tetrazol-5-yl | n-propyl | —N(benzyl)CO₂isobutyl |
| 1H-tetrazol-5-yl | n-propyl | —N(4-methoxybenzyl)(5-methyl-pentanoyl) |
| 1H-tetrazol-5-yl | n-propyl | —N(benzyl)CO₂CH₃ |
| 1H-tetrazol-5-yl | n-propyl | —N(benzyl)CO₂CH₂CH₃ |
| 1H-tetrazol-5-yl | n-propyl | —N(n-pentyl)CO-4-pyridyl |
| 1H-tetrazol-5-yl | n-propyl | —N(benzyl)(benzoyl) |

TABLE III-continued

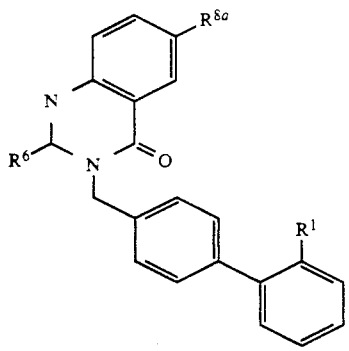

| R¹ | R⁶ | R⁸ᵃ |
|---|---|---|
| 1H-tetrazol-5-yl | n-butyl | —SO₂N(benzyl)₂ |
| 1H-tetrazol-5-yl | n-propyl | —N(benzyl)CON(CH₃)(CH₂CH₃) |
| 1H-tetrazol-5-yl | n-propyl | —N(n-pentyl)CO-2-furanyl |
| 1H-tetrazol-5-yl | n-propyl | —N(4-benzyloxybenzyl)(2-methylpentanoyl) |
| 1H-tetrazol-5-yl | n-propyl | —N(4-hydroxybenzyl)(2-methylpentanoyl) |
| 1H-tetrazol-5-yl | ethyl | —N(4-fluorobenzyl)(benzoyl) |
| 1H-tetrazol-5-yl | ethyl | —N(n-pentyl)SO₂-butyl |
| 1H-tetrazol-5-yl | n-propyl | —N(CH₃)CO₂-isobutyl |
| 1H-tetrazol-5-yl | n-propyl | —N(benzyl)CO₂-isobutyl |
| 1H-tetrazol-5-yl | ethyl | —N(benzyl)CONH-propyl |
| 1H-tetrazol-5-yl | cyclopropyl | —N(n-pentyl)benzoyl |
| 1H-tetrazol-5-yl | cyclopropyl | —N(benzyl)benzoyl |
| 1H-tetrazol-5-yl | propyl | —N(butyl)CO-4-pyridyl |
| 1H-tetrazol-5-yl | methyl | —N(benzyl)benzoyl |
| 1H-tetrazol-5-yl | ethyl | —N(benzyl)SO₂-propyl |
| 1H-tetrazol-5-yl | isopropyl | —N(benzyl)benzoyl |
| 1H-tetrazol-5-yl | propyl | —N(n-pentyl)CO-4-pyridyl |
| 1H-tetrazol-5-yl | ethyl | —N(benzyl)CO-4-pyridyl |
| 1H-tetrazol-5-yl | propyl | —N(n-pentyl)(4-thiomethylbenzoyl) |
| 1H-tetrazol-5-yl | ethyl | —N(benzyl)(2-chlorobenzoyl) |
| 1H-tetrazol-5-yl | ethyl | —N(2-chlorobenzyl)(2-chlorobenzoyl) |
| 1H-tetrazol-5-yl | ethyl | —N(n-pentyl)(4-sulfonylmethylbenzoyl) |
| 1H-tetrazol-5-yl | propyl | —N(n-pentyl)(4-sulfonylmethylbenzoyl) |
| 1H-tetrazol-5-yl | propyl | —N(CH₂CH₂CHO)(benzyoyl) |
| 1H-tetrazol-5-yl | ethyl | —N(2-chlorobenzyl)(benzoyl) |
| 1H-tetrazol-5-yl | propyl | —N(propyl)(4-fluorobenzoyl) |
| 1H-tetrazol-5-yl | ethyl | —N(4-methylbutyl)(benzoyl) |
| 1H-tetrazol-5-yl | isopropyl | —N(2-chlorobenzyl(benzoyl) |
| 1H-tetrazol-5-yl | H | —N(benzyl)(benzoyl) |
| 1H-tetrazol-5-yl | H | —N(2-chlorobenzyl)(benzoyl) |
| 1H-tetrazol-5-yl | ethyl | —N(4-chlorobenzyl)(benzoyl) |
| 1H-tetrazol-5-yl | ethyl | —N(2-fluorobenzyl)(benzoyl) |
| 1H-tetrazol-5-yl | ethyl | —N(3-chlorobenzyl)(benzoyl) |
| 1H-tetrazol-5-yl | isobutyl | —N(benzyl)(benzoyl) |
| 1H-tetrazol-5-yl | isobutyl | —N(2-chlorbenzyl)(benzoyl) |
| 1H-tetrazol-5-yl | methyl | —N(2-chlorbenzyl)(benzoyl) |
| 1H-tetrazol-5-yl | methyl | -(benzyl)CO-4-pyridyl |
| 1H-tetrazol-5-yl | methyl | —N(4-methylbut-2-enyl)CO-4-pyridyl |
| 1H-tetrazol-5-yl | propyl | —N(CH₂-4-pyridyl)CO₂-n-propyl |
| 1H-tetrazol-5-yl | propyl | —N(n-pentyl)CO-2-thienyl |
| 1H-tetrazol-5-yl | ethyl | —N(benzyl)(4-iodobenzoyl) |
| 1H-tetrazol-5-yl | ethyl | —N(2-iodobenzyl)(benzoyl) |
| 1H-tetrazol-5-yl | ethyl | —N(benzyl)CO-2-thienyl |
| 1H-tetrazol-5-yl | propyl | —N(4-fluorobenzyl)CON(CH₃)(isopropyl). |

The compounds of Formula (I) can be synthesized using the reactions and techniques described in published European Patent Application EP 411,766 (Merck & Co. Inc.) and the schemes described below. The above mentioned application discloses the compounds of this invention where they are alleged to be angiotensin II receptor antagonists useful in the treatment of hypertension and ocular hypertension.

The morpholinyl and piperazinyl-substituted quinazolinone compounds of this invention are prepared in accordance with the following Reaction Scheme:

SCHEME 1

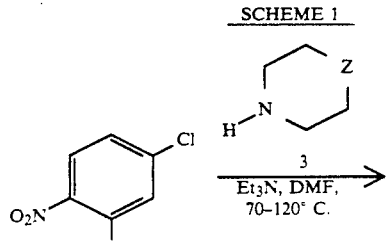

15

-continued
SCHEME 1

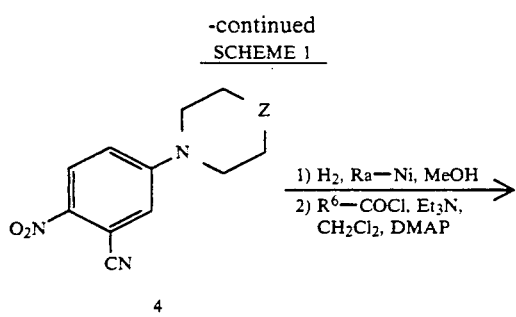

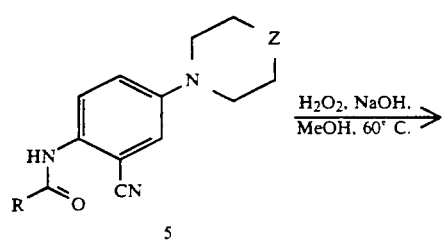

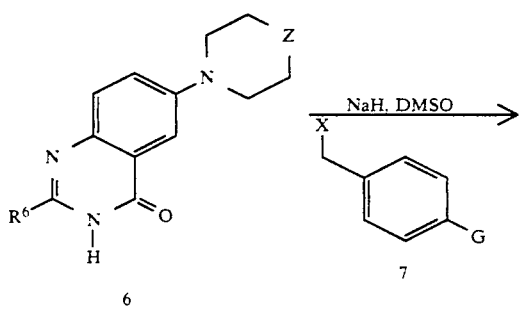

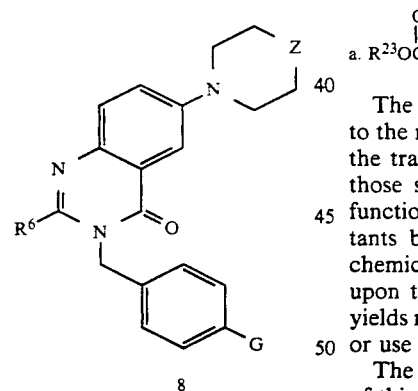

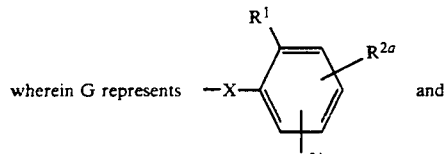

Z represents —O— or —NR$^{24}$—.

Compounds of Formula (I) wherein R$^1$ is —SO$_2$NHCO$_2$R$^{23}$ may be prepared by reacting an appropriate chloroformate with the sulfonamide (9) in pyridine or in the presence of DBU in THF to afford the desired compound (10), as outlined in Scheme 2.

16

SCHEME 2

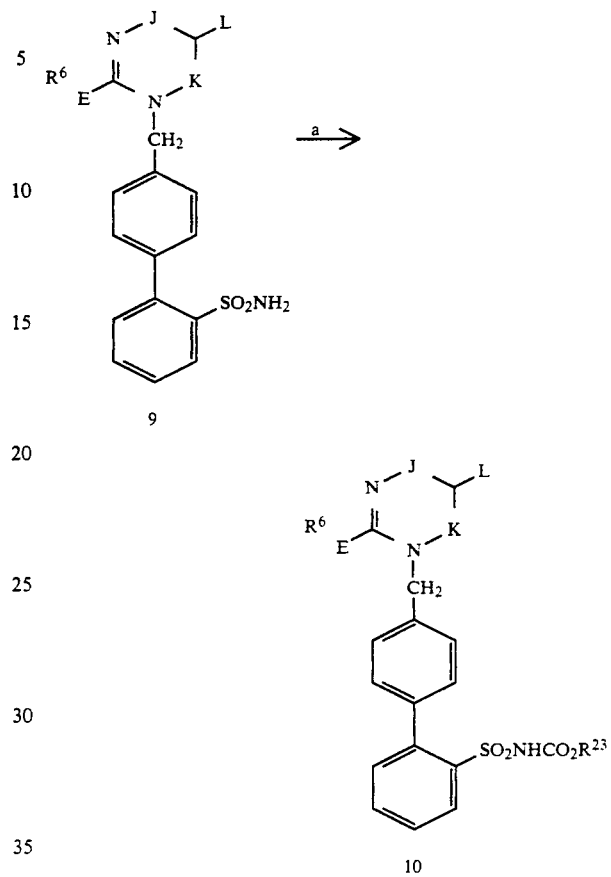

a. R$^{23}$OCCl, pyridine or DBU, THF

The reactions are performed in a solvent appropriate to the reagents and materials employed and suitable for the transformation being effected. It is understood by those skilled in the art of organic synthesis that the functionality present on the heterocycle and in the reactants being employed should be consistent with the chemical transformations being conducted. Depending upon the reactions and techniques employed, optimal yields may require changing the order of synthetic steps or use of protecting groups followed by deprotection.

The compounds useful in the novel method treatment of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glutamine, salts with amino acids like arginine, lysine, and the like. Also, salts with organic and inorganic acids may be prepared; e.g., HCl, HBr, H$_2$SO$_4$, H$_3$PO$_4$, methanesulfonic, toluenesulfonic, maleic, fumaric, camphorsulfonic.

The salts can be formed by conventional means, such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Neurotensin is a peptide hormone and the assays described below have been developed to identify neurotensin antagonists and to determine their efficacy in vitro. The following three assays have been employed for that purpose.

RAT FOREBRAIN RECEPTOR ASSAY

Male rats are sacrificed by decapitation following ether anesthetization. Forebrains are homogenized using a polytron in 20 volumes 50 mM Tris HCl, pH 7.4, and centrifuged at 50,000×g for 20 min. The final pellet is washed twice by rehomogenization and centrifugation as before. The final pellet is resuspended at a concentration of 8 mg tissue (wet weight) per 0.750 ml of 50 $\mu$M Tris HCl, pH 7.4, which also contains 1 mM EDTA, 4 $\mu$g/ml bacitracin, 5 $\mu$M levocabastine HCl, 1 mM phenanthroline, 10 $\mu$g/ml soybean trypsin inhibitor and 100 $\mu$M phenyl methyl sulfonyl fluoride. Assay tubes (13×100 polypropylene) receive 1) 100 $\mu$l buffer or 10 $\mu$M neurotensin (for non-specific binding) 2) 100 $\mu$l of 60 pM [$^{125}$I]neurotensin 3) 20 $\mu$l test compounds 4) 750 $\mu$l tissue suspension and 5) enough buffer to bring final volume to 1 ml. After 30 minutes at room temp, the samples are filtered using a Brandel M24 cell harvestor with GF/B filtermats that have been presoaked in 0.2% polyethyleneimine for 2 hours. The tubes are rinsed with 3×4 ml of ice cold 10 mM Tris buffer (pH 7.4 at room temperature). The filter discs are placed in 12×75 mM polypropylene tubes for counting on a Packard Multi-Prias gamma counter.

HUMAN HT-29 CELL MEMBRANE ASSAY

HT-29 cells were routinely grown in 255 cm$^2$ Costar tissue culture flasks at 37° C. in a humidified atmosphere of 5% CO$_2$/95% air in Dulbecco's modified Eagle's medium with high glucose containing 50 U/ml penicillin, 50 $\mu$g/ml streptomycin, 5% fetal bovine serum and 5% newborn calf serum. Cells were subcultured with 0.25% trypsin at a ratio of 1:6 with confluence being reached at 48 to 72 hrs. Cells from confluent flasks (approx. 1×10$^8$ cells/flask) were harvested by scraping. The cells were pelleted by centrifugation (1000×g, 5 min), resuspended in 50 mM Tris HCl, pH 7.4, and homogenized with a polytron (setting 7 for 10 sec.). Cell membranes were washed twice by centrifugation (50,000×g, 15 min) and rehomogenization. The resulting pellet was either frozen at −70° C. for future use or run directly in the assay by resuspending at a concentration of 0.5×10$^6$ cells per 0.750 ml of assay buffer (50 mM Tris HCl, pH 7.4, containing 1 mM EDTA, 40 $\mu$g/ml bacitracin, 1 mM phenanthroline, 10 $\mu$g/ml soybean trypsin inhibitor and 100 $\mu$M phenylmethylsulfonyl fluoride).

Assay tubes (13×100 polypropylene) receive 1) 100 $\mu$l buffer or 10 $\mu$M neurotensin (for non-specific binding) 2) 100 $\mu$l of 60 pM [$^{125}$I]neurotensin 3) 20 $\mu$l test compounds 4) 750 $\mu$l cell membrane suspension an 5) enough buffer to bring final volume to 1 ml. After 30 minutes at room temperature, the samples are filtered using a Brandel M24 cell harvestor with GF/B filtermats that have been presoaked in 0.2% polyethyleneimine for 2 hours. The tubes are rinsed with 3×4 ml of ice cold 10 mM Tris buffer (pH 7.4 at room temperature). The filter discs are placed in 12×75 mM polypropylene tubes for counting on a Packard Multi-Prias gamma counter. [The above assay is derived from the assay described in Kitabgi, P. et al., Molecular Pharmacology, 18, 11-19 (1980)].

NEUROTENSIN BINDING ASSAY TO HUMAN FRONTAL CORTEX

Post-mortem human brain is obtained through the National Disease Research Interchange (Philadelphia, PA). The donors were without psychiatric or neurological abnormalities. Frontal cortex is dissected free of white matter and homogenized using a polytron in 20 volumes 50 mM Tris HCl, pH 7.4, and centrifuged at 50,000×g for 20 min. The resulting pellet is washed twice by rehomogenization and centrifugation as before. The final pellet is resuspended at a concentration of 8 mg tissue (wet weight) per 0.750 ml of 50 mM Tris HCl, pH 7.4, which also contains 1 mM EDTA, 4 $\mu$g/ml bacitracin, 1 mM phenanthroline, 10 $\mu$g/ml soybean trypsin inhibitor and 100 $\mu$M phenyl methyl sulfonyl fluoride. Assay tubes (13×100 polypropylene) receive 1) 100 $\mu$l buffer or 10 $\mu$M neurotensin (for non-specific binding) 2) 100 $\mu$l of 60 pM [$^{125}$I]neurotensin 3) 20 $\mu$l test compounds 4) 750 $\mu$l tissue suspension and 5) enough buffer to bring final volume to 1 ml. After 30 minutes at room temp, the samples are filtered using a Brandel M24 cell harvestor with GF/B filtermats that have been presoaked in 0.2% polyethyleneimine for 2 hours. The tubes are rinsed with 3×4 ml of ice cold 10 mM Tris buffer (pH 7.4 at room temperature). The filter discs are placed in 12×75 mM polypropylene tubes for counting on a Packard Multu-Prias gamma counter.

Using the methodology described above, representative compounds of the invention were evaluated and all were found to exhibit an activity of at least IC$_{50}$<50 $\mu$M thereby demonstrating and confirming the utility of the compounds of the invention as effective neurotensin antagonists.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following list of compounds are prepared according to the procedures disclosed in published European Patent Application EP 411,766:

6-Isopropyl-2-butyl-3-[(2'-(N-triphenylmethyltetrazol-5-yl)biphen-4-yl)methyl]quinazolin-4(3H)-one 6-Nitro-2-butyl-3-[(2'-(N-triphenylmethyl-tetrazol-5-yl)biphen-4-yl)methyl]quinazolin-4(3H)-one 6-Nitro-2-propyl-3-[(2'-(N-triphenylmethyl-tetrazol-5-yl)biphen-4-yl)methyl]quinazolin-4(3H)-one 2-Butyl-3-[(2'-(N-triphenylmethyl-tetrazol-5-yl)-biphen-4-yl)methyl]-6-thiomethylquinazolin-4(3H)-one 2-Butyl-3-(4'-fluoro-2'-(N-triphenylmethyltetrazol-5-yl)biphen-4-yl)methyl-6-isopropylquinazolin-4(3H)-one 2-Butyl-6-methyl-3-[(2'-nitrobiphen-4-yl)methyl]-quinazolin-4(3H)-one 3-[(2'-Aminobiphen-4-yl)methyl]-2-butyl-6-methyl-quinazolin-4(3H)-one 2-Butyl-6-methyl-3-[(2'-trifluoromethylsulfonamidobiphen-4-yl)-methyl]quinazolin-4(3H)-one 6-Acetoxymethyl-2-butyl-3-[(2'-(N-triphenylmethyltetrazol-5-yl)biphen-4-yl)methyl]quinazolin-4(3H)-one 5-Acetoxymethyl-2-butyl-3-[(2'-(N-triphenylmethyltetrazol-5-yl)biphen-4-yl)methyl]quinazolin-4(3H)-one 2-Butyl-7-chloro-3-[(2'-(N-triphenylmethyl-tetrazol-5-yl)biphen-4-yl)methyl]quinazolin-4(3H)-one 2-Butyl-6-ethyl-3-[(2'-(N-triphenylmethyl-tetrazol-5yl)-biphen-4-yl)methyl]quinazolin-4(3H)-one 6-Amino-2-butyl-3-[(2'-(t-butoxycarbonyl)biphen-4-yl)methyl]quinazolin-4(3H)-one 6-Amino-2-butyl-3-[(2'triphenylmethyl-tetrazol-5-yl)biphen-4-yl)methyl]quinazolin-4(3H)-one 6-Amino-2-propyl-3-[(2'-(N-triphenylmethyl-tetrazol-5-yl)biphen-4-yl)methyl]quinazolin-4(3H)-one 6-Acetamido-2-butyl-3-[(2'-triphenylmethyl-tetrazol-5-yl)biphen-4-yl)methyl]quinazolin-4(3H)-one 2-Butyl-3-[(2'-(N-triphenylmethyl-tetrazol-5-yl)biphen-4-yl)methyl]-6-valeroylamidoquinazolin-4(3H)-one 2-Butyl-6-(N-carbobenzyloxy)amino-3-[(2'-(N-triphenylmethyl-tetrazol-5-yl)biphen-4-yl)methyl]-quinazolin-4(3H)-one 6-(N-Isopropylcarbamoyl)amino-2-propyl-3-[(2'-(N-triphenylmethyl-tetrazol-5-yl)biphen-4-yl)methyl]-quinazolin-4(3H)-one 6-(N-Benzyl)amino-2-butyl-3-[(2'-(N-triphenylmethyltetrazol-5-yl)biphen-4-yl)methyl]quinazolin-4(3H)-one 2-Butyl-6-(N,N-dimethyl)amino-3-[(2'-(N-triphenylmethyl-tetrazol-5-yl)biphen-4-yl)methyl]quinazolin-4(3H)-one 2-Butyl-6-(N-isopropylcarbamoyl)amino-3-[(2'-(N-triphenylmethyl-tetrazol-5-yl)biphen-4-yl)methyl]-quinazolin-4(3H)-one 2-Butyl-6-ethyl-3-[(2'-(tetrazol-5-yl)biphen-4-yl)methyl]quinazolin-4(3H)-one 2-Butyl-7-chloro-3-[(2'-(tetrazol-5-yl)biphen-4-yl)methyl]quinazolin-4(3H)-one 2-Butyl-6-isopropyl-3-[(2'-(tetrazol-5-yl)biphen-4-yl)methyl]quinazolin-4(3H)-one 6-Acetoxymethyl-2-butyl-3-[(2'-(tetrazol-5-yl)biphen-4-yl)methyl]quinazolin-4(3H)-one 5-Acetoxymethyl-2-butyl-3-[(2'-(tetrazol-5-yl)biphen-4-yl)methyl]quinazolin-4(3H)-one 2-Butyl-6-nitro-3-[(2'-(tetrazol-5-yl)biphen-4-yl)methyl]quinazolin-4(3H)-one 6-Amino-2-butyl-3-[(2'-(tetrazol-5-yl)biphen-4-yl)methyl]quinazolin-4(3H)-one 6-(N-Benzyl)amino-2-butyl-3-[(2'-(tetrazol-5-yl)biphen-4-yl)methyl]quinazolin-4(3H)-one 2-Butyl-6-(N,N-dimethyl)amino-3-[(2'-(tetrazol-5-yl)biphen-4-yl)methyl]quinazolin-4(3H)-one 6-Acetamido-2-butyl-3-[(2'-(tetrazol-5-yl)biphen-4-yl)methyl]quinazolin-4(3H)-one 2-Butyl-3-[(2'-(tetrazol-5-yl)biphen-4-yl)methyl]-6-valeroylamidoquinazolin-4(3H)-one 2-Butyl-6-(N-carbobenzyloxy)amino-3[(2'-(tetrazol-5-yl)biphen-4-yl)methyl]quinazolin-4(3H)-one 2-Butyl-6-(N-isopropylcarbamoyl)amino-3-[(2'-tetrazol-5-yl)biphen-4-yl)methyl]quinazolin-4(3H)-one 2-Butyl-3-[(2'-(tetrazol-5-yl)biphen-4-yl)methyl]-6-thiomethylquinazolin-4(3H)-one 6-(N-Isopropylcarbamoyl)amino-2-propyl-3-[(2'-(tetrazol-5-yl)biphen-4-yl)methyl]quinazolin-4(3H)-one 2-Butyl-3-(4'-fluoro-2'-(tetrazol-5-yl)biphen-4-yl)methyl-6-isopropylquinazolin-4(3H)-one 2-Butyl-6-methyl-3-[(2'-(tetrazol-5-yl)biphen-4-yl)methyl]quinazolin-4(3H)-one 2-Butyl-3-[(2'-(tetrazol-5-yl)biphen-4-yl)methyl]-quinazolin-4(3H)-one 6-Methyl-2-propyl-3-[(2'-(tetrazol-5-yl)biphen-4-yl)methyl]quinazolin-4(3H)-one 2-Butyl-6-hydroxymethyl-3[(2'-(tetrazol -5-yl)biphen-4-yl)methyl]quinazolin-4(3H)-one 2-Butyl-5-hydroxymethyl-3-[(2'-(tetrazol-5-yl)biphen-4-yl)methyl]quinazolin-4(3H)-one 2-Butyl-6-carboxy-3-[(2'-(tetrazol-5-yl)biphen-4-yl)methyl]quinazolin-4(3H)-one 2-Butyl-5-carboxy-3-[(2'-(tetrazol-5-yl)biphen-4-yl)methyl]quinazolin-4(3H)-one 2-Butyl-6-carbomethoxy-3-[(2'-(tetrazol-5-yl)biphen-4-yl)-methyl]quinazolin-4(3H)-one 2-Butyl-5-carbomethoxy-3-[(2'-(tetrazol-5-yl)biphen-4-yl)-methyl]quinazolin-4(3H)-one 2-Butyl-6-(methylsulfonyl)-3-[(2'-(tetrazol-5-yl)biphen-4-yl)methyl]quinazolin-4(3H)-one 2-Butyl-6-(methylsulfinyl)-3-[(2'-(tetrazol-5-yl)biphen-4-yl)methyl]quinazolin-4(3H)-one In a similar fashion the following 1,2-dialkylated quinazolin-4(1H)-ones may be prepared:

2-Butyl-1-[(2'-(tetrazol-5-yl)biphen-4-yl)methyl]-quinazolin-4(1H)-one;

2-Propyl-1-[(2'-(tetrazol-5-yl)biphen-4-yl)methyl]-quinazolin-4(1H)-one;

2-Butyl-6-methyl-1-[(2'-(tetrazol-5-yl)biphen-4-yl)methyl]quinazolin-4(1H)-one;

6-Methyl-2-pentyl-1-[(2'-(tetrazol-5-yl)biphen-4-yl)methyl]quinazolin-4(1H)-one;

2-Butyl-6-methyl-1-[(2'-(tetrazol-5-yl)biphen-4-yl)methyl]quinazolin-4(1H)-one;

2-Butyl-5-methyl-1-[(2'-(tetrazol-5-yl)biphen-4-yl)methyl]quinazolin-4(1H)-one;

2-Butyl-7-methyl-1-[(2'-(tetrazol-5-yl)biphen-4-yl)methyl]quinazolin-4(1H)-one;

2-Butyl-6-nitro-1-[(2'-(tetrazol-5-yl)biphen-4-yl)methyl]quinazolin-4(1H)-one.

What is claimed is:

1. A method of treating central nervous system disorders which comprises administering to a patient in need of such treatment a therapeutically effective amount of a compound of structural formula:

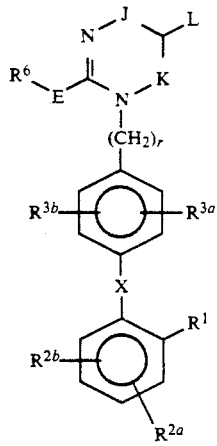

or a pharmaceutically acceptable salt thereof, wherein:
L is connected with J or K to form an aromatic ring as defined below;
J is —C(=M)— or J and L are connected together to form a 6 carbon aromatic ring substituted with $R^{7a}$, $R^{7b}$, $R^{8a}$ and $R^{8b}$;
K is —C(=M)— or K and L are connected together to form a 6 carbon aromatic ring substituted with $R^{7a}$, $R^{7b}$, $R^{8a}$ and $R^{8b}$, provided that only one of J and K is —C(=M)—;
M is O or $NR^{22}$;
$R^1$ is
  (a) —$NHSO_2R^{23}$,
  (b) —$NHSO_2NHCOR^{23}$,
  (c) —$NHCONHSO_2R^{23}$,
  (d) —$SO_2NHR^{23}$,
  (e) —$SO_2NHCOR^{23}$,
  (f) —$SO_2NHCONR^4R^{23}$,
  (g) —$SO_2NHCOOR^{23}$,
  (h) —$SO_2NHOR^{23}$,
  (i) —$CH_2SO_2NHCOR^{23}$,
  (j) —$CH_2SO_2NHCONHR^{23}$,
  (k) —$CO_2H$, or
  (l) —1H-tetrazol-5-yl;
$R^{2a}$ and $R^{2b}$ are each independently
  (a) H,
  (b) Cl, Br, I, F,
  (c) $CF_3$,
  (d) $C_1$-$C_6$-alkyl,
  (e) $C_1$-$C_6$-alkoxy,
  (f) $C_1$-$C_6$-alkyl-S—,
  (g) $C_2$-$C_6$-alkenyl,
  (h) $C_2$-$C_6$-alkynyl,
  (i) $C_3$-$C_7$-cycloalkyl,
  (j) aryl, or
  (k) aryl-$C_1$-$C_6$-alkyl;
$R^{3a}$ is
  (a) H,
  (b) Cl, Br, I, F,
  (c) $C_1$-$C_6$-alkyl,
  (d) $C_1$-$C_6$-alkoxy, or
  (e) $C_1$-$C_6$-alkoxyalkyl;
$R^{3b}$ is
  (a) H,
  (b) Cl, Br, I, F,
  (c) $C_1$-$C_6$-alkyl,
  (d) $C_3$-$C_7$-cycloalkyl,
  (e) $C_1$-$C_6$-alkoxy,
  (f) $CF_3$,
  (g) $C_2$-$C_6$-alkenyl, or
  (h) $C_2$-$C_6$-alkynyl;
$R^4$ is
  (a) H,
  (b) $C_1$-$C_6$-alkyl,
  (c) aryl, wherein aryl is phenyl or naphthyl, either unsubstituted or substituted with one or two substituents selected from the group consisting of halogen, $N(R^4)_2$, $CO_2R^4$, $C_1$-$C_4$-alkyl, $C_1$-$C_4$-alkoxy, $NO_2$, $CF_3$, $C_1$-$C_4$-alkylthio, and OH;
  (d) aryl-$C_1$-$C_6$ alkyl, or
  (e) heteroaryl, wherein heteroaryl is an unsubstituted, monosubstituted or disubstituted five or six membered aromatic ring selected from thiazole, imidazole, pyrazole, oxazole, pyridine, thiazine, pyrazine, pyrimidine wherein the substituents are members selected from the group consisting of —OH, —SH, —$C_1$-$C_4$-alkyl, —$C_1$-$C_4$-alkoxy, —$CF_3$, Cl, Br, F, I, —$NO_2$, —$CO_2H$, —$CO_2$—($C_1$-$C_4$-alkyl), —$NH_2$, —NH($C_1$-$C_4$-alkyl) and —N($C_1$-$C_4$-alkyl)$_2$;
E is a single bond, —$NR^{13}(CH_2)_s$—, —$S(O)_x(CH_2)_s$— where x is 0 to 2 and s is 0 to 5, —CH(OH)—, —O—, or —CO—;
$R^6$ is
  (a) H,
  (b) aryl,
  (c) $C_1$-$C_6$-alkyl, $C_2$-$C_5$-alkenyl or $C_2$-$C_5$-alkynyl each of which is unsubstituted or substituted with a substituent selected from the group consisting of aryl, Cl, Br, I, F, $C_3$-$C_7$-cycloalkyl, —$NH_2$, —NH($C_1$-$C_4$-alkyl), —$OR^4$, —N($C_1$-$C_4$-alkyl)$_2$, —NH—$SO_2R^4$, —$COOR^4$, and —$SO_2NHR^9$; or
  (d) heteroaryl, or
  (e) $C_3$-$C_7$-cycloalkyl;
$R^{7a}$ and $R^{7b}$ are independently
  (a) H,
  (b) $C_1$-$C_6$-alkyl, $C_2$-$C_6$-alkenyl or $C_2$-$C_6$-alkynyl,
  (c) Cl, Br, I, F,
  (d) $CF_3$,
  (e) when $R^{7a}$ and $R^{7b}$ are bonded to adjacent carbon atoms, they joined to form a phenyl ring, or
  (f) aryl;
$R^{8a}$ and $R^{8b}$ are independently
  (a) H,
  (b) $C_1$-$C_6$-alkyl, unsubstituted or substituted with a substituent selected from the group consisting of —OH, -guanidino, $C_1$-$C_4$-alkoxy, —$N(R^4)_2$, $COOR^4$, —$CON(R^4)_2$, —O—$COR^4$, -aryl, -heteroaryl, —$S(O)_x$—$R^{23}$, -tetrazol-5-yl, —$CONHSO_2R^{23}$, —$SO_2NH$-heteroaryl, —$SO_2NHCOR^{23}$, —$PO(OR^4)_2$, —$PO(OR^4)R^9$, —$SO_2NH$-CN, —$NR^{10}COOR^{23}$, morpholino, N—($C_1$-$C_6$-alkyl)piperazine, and —$COR^4$,
  (c) —CO-aryl,
  (d) —$C_3$-$C_7$-cycloalkyl,
  (e) Cl, Br, I, F,
  (f) —OH,
  (g) —$OR^{23}$,
  (h) —$C_1$-$C_4$-perfluoroalkyl,
  (i) —$S(O)_x$—$R^{23}$,
  (j) —$COOR^4$,
  (k) —$SO_3H$,
  (l) —$NR^4R^{23}$, (m) —NR⁴COR²³,
(n) —NR⁴COOR²³,
(o) —SO₂NR⁹R¹⁰,
(p) —NO₂,
(q) —NR⁴SO₂R²³,
(r) —NR⁴CONR⁴R²³,

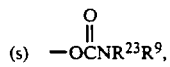
(s) —OCNR²³R⁹, (t) -aryl or -heteroaryl as defined above,
(u) —NHSO₂CF₃,
(v) —SO₂NH-heteroaryl,
(w) —SO₂NHCOR²³,
(x) —CONHSO₂R²³,
(y) —PO(OR⁴)₂,
(z) —PO(OR⁴)R⁹,
(aa) -tetrazol-5-yl,
(bb) —CONH(tetrazol-5-yl),
(cc) —COR⁴,
(dd) —SO₂NHCN, (ee)
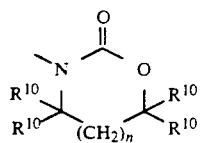
where n = 0 or 1.

(ff) —CO-heteroaryl,
(gg) —NR⁴SO₂NR²³R⁹,
(hh) —N[CH₂CH₂]₂NR²⁴, wherein R²⁴ is C₁-C₆-alkyl, —C₃-C₇-cycloalkyl, —CONR⁹R¹⁰, -heteroaryl, -phenyl, —CO—C₃-C₇-cycloalkyl, —CO—C₁-C₆-alkyl, —SO₂—C₁-C₆-alkyl, or —SO₂—C₃-C₇-cycloalkyl, or
(ii) —N[CH₂CH₂]₂O;

R⁹ is H, C₁-C₅-alkyl, aryl or arylmethyl;
R¹⁰ is H, C₁-C₄-alkyl;
R¹¹ is H, C₁-C₆-alkyl, C₁-C₄-alkenyl, C₁-C₄-alkoxy alkyl, or

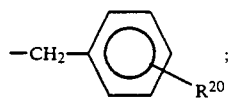

R¹² is —CN, —NO₂, —CF₃ or —CO₂R⁴;
R¹³ is H, (C₁-C₄-alkyl)CO—, C₁-C₆-alkyl, allyl, C₃-C₆-cycloalkyl, aryl or arylmethyl;
R¹⁴ is H, C₁-C₈-alkyl, C₁-C₈-perfluoroalkyl, C₃-C₆-cycloalkyl, aryl or arylmethyl;
R¹⁵ is H, C₁-C₆-alkyl;
R¹⁶ is H, C₁-C₆-alkyl, C₃-C₆-cycloalkyl, aryl or arylmethyl;
R¹⁷ is —NR⁹R¹⁰, —OR¹⁰, —NHCONH₂, —NHCSNH₂,

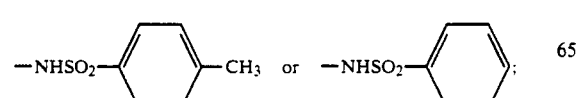

R¹⁸ and R¹⁹ are independently C₁-C₄-alkyl or taken together are —(CH₂)_q— where q is 2 or 3;
R²⁰ is H, —NO₂, —NH₂, —OH or —OCH₃;
R²¹ is H, aryl, or C₁-C₄-alkyl optionally substituted with aryl, —NH₂, —NH(C₁-C₄-alkyl), —N(-C₁-C₄-alkyl)₂, —CO₂R⁴, —OH, —SO₃H, or —SO₂NH₂;
R²² is
(a) aryl,
(b) heteroaryl,
(c) C₁-C₆-alkyl unsubstituted or substituted with a substituent selected from the group consisting of aryl, heteroaryl, —OH, —NH₂, —NH(C₁-C₄-alkyl), —N(C₁-C₄-alkyl)₂, —CO₂R⁴, Cl, Br, F, I, and —CF₃, or
(d) perfluoro-C₁-C₄-alkyl;
R²³ is
(a) aryl,
(b) heteroaryl,
(c) C₃-C₇-cycloalkyl,
(d) C₁-C₈-alkyl wherein alkyl is unsubstituted or substituted with one or two substituents selected from the group consisting of aryl, heteroaryl, —OH, —SH, C₁-C₄-alkyl, —O(C₁-C₄-alkyl), —S(C₁-C₄-alkyl), —CF₃, Cl, Br, F, I, —NO₂, —CO₂H, —CO₂—C₁-C₄-alkyl, —NH₂, —NR⁴CO₂R²², —NH(C₁-C₄-alkyl), —N(C₁-C₄-alkyl)₂, —PO₃H₂, —PO(OH)(O—C₁-C₄-alkyl), —PO(OR⁴)R⁹, —NR⁴COR²², —CONR⁴R²², —OCONR⁴R²², —SO₂NR⁴R²², or —NR⁴SO₂R²², or
(e) perfluoro-C₁-C₄-alkyl;
X is
(a) a carbon-carbon single bond,
(b) —CO—,
(c) —O—,
(d) —S—, (e) 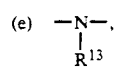

(f) 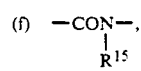

(g) 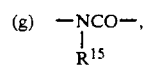

(h) —OCH₂—,
(i) —CH₂O—
(j) —SCH₂—,
(k) —CH₂S—,
(l) —NHC(R⁹)(R¹⁰),
(m) —NR⁹SO₂—,
(n) —SO₂NR⁹—,
(o) —C(R⁹)(R¹⁰)NH—,
(p) —CH=CH—,
(q) —CF=CF—,
(r) —CH=CF—,
(s) —CF=CH—,
(t) —CH₂CH₂—,
(u) —CF₂CF₂—, (v) 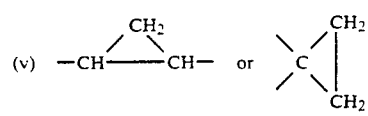

-continued (w) 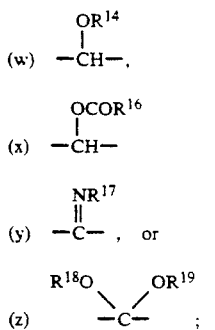

(x) —CH(OCOR$^{16}$)—

(y) —C(=NR$^{17}$)—, or (z) —C(OR$^{18}$)(OR$^{19}$)— ;

r is 1 or 2.

2. The method of claim 1 wherein:
J is —C(O)—;
K and L are connected together to form a 6 carbon aromatic ring substituted with R$^{7a}$, R$^{7b}$, R$^{8a}$ and R$^{8b}$;
R$^1$ is
  (a) —NHSO$_2$R$^{23}$,
  (b) —NHSO$_2$NHCOR$^{23}$,
  (c) —NHCONHSO$_2$R$^{23}$,
  (d) —SO$_2$NHR$^{23}$,
  (e) —SO$_2$NHCOR$^{23}$,
  (f) —SO$_2$NHCONR$^4$R$^{23}$,
  (g) —SO$_2$NHCOOR$^{23}$,
  (h) —SO$_2$NHOR$^{23}$,
  (i) —CH$_2$SO$_2$NHCOR$^{23}$,
  (j) —CH$_2$SO$_2$NHCONHR$^{23}$,
  (k) —CO$_2$H, or
  (l) —1H-tetrazol-5-yl;
R$^{2a}$ is H;
R$^{2b}$ is H, F, Cl, CF$_3$, C$_1$-C$_6$-alkyl, C$_2$-C$_4$-alkenyl or C$_2$-C$_4$-alkynyl, aryl or aryl-C$_1$-C$_6$-alkyl;
R$^{3a}$ is H;
R$^{3b}$ is H, F, Cl, CF$_3$, C$_1$-C$_4$-alkyl, C$_2$-C$_4$-alkenyl, C$_2$-C$_4$-alkynyl or C$_5$-C$_6$-cycloalkyl;
E is a single bond, —O—, —S—, or —SO$_2$—;
R$^6$ is
  (a) C$_1$-C$_5$-alkyl either unsubstituted or substituted with a substituent selected from the group consisting of C$_3$-C$_5$-cycloalkyl, Cl, —O—CH$_3$, —OC$_2$H$_5$, or F,
  (b) C$_2$-C$_5$-alkenyl or C$_2$-C$_5$-alkynyl,
  (c) C$_3$-C$_5$-cycloalkyl, or
  (d) aryl;
R$^{7a}$ and R$^{7b}$ are independently
  (a) H;
  (b) C$_1$-C$_6$-alkyl, or
  (c) aryl;
R$^{8a}$ and R$^{8b}$ are independently
  (a) H,
  (b) C$_1$-C$_6$-alkyl or substituted C$_1$-C$_4$-alkyl with an COOR$^4$, OCOR$^{4a}$, OH, or aryl,
  (c) —OH,
  (d) —NO$_2$,
  (e) —NR$^4$COR$^{23}$,
  (f) —C$_1$-C$_4$-alkoxy,
  (g) —NR$^4$CO$_2$R$^{23}$,
  (h) —NR$^4$R$^{23}$,
  (i) —Cl, F, Br,
  (j) —CF$_3$,
  (k) —CO$_2$R$^4$,
  (l) —CO-aryl,
  (m) —S(O)$_x$—C$_1$-C$_4$-alkyl,
  (n) —SO$_2$—NH—C$_1$-C$_4$-alkyl,
  (o) —SO$_2$—NH-aryl,
  (p) —NR4SO$_2$CH$_3$,
  (q) —aryl,
  (r) —NR$^4$CONR$^4$R$^{23}$,
  (s) —N[CH$_2$CH$_2$]$_2$R$^{24}$, or
  (t) —N[CH$_2$CH$_2$]$_2$O;
X is a single bond and;
r is one.

3. The method of claim 2 wherein:
R$^1$ is:
  (a) —NHSO$_2$R$^{23}$,
  (b) —NHSO$_2$NHCOR$^{23}$,
  (c) —NHCONHSO$_2$R$^{23}$,
  (d) —SO$_2$NHR$^{23}$,
  (e) —SO$_2$NHCOR$^{23}$,
  (f) —SO$_2$NHCONR$^4$R$^{23}$,
  (g) —SO$_2$NHCOOR$^{23}$,
  (h) —SO$_2$NHOR$^{23}$,
  (i) —CH$_2$SO$_2$NHCOR$^{23}$,
  (j) —CH$_2$SO$_2$NHCONHR$^{23}$,
  (k) —1H-tetrazol-5-yl, or
  (l) —CO$_2$H;
E is a single bond;
r is one;
R$^6$ is —C$_1$-C$_4$-alkyl, -cyclopropyl, —CH$_2$CH$_2$CH$_2$CF$_3$, —CH$_2$CH$_2$CF$_3$, —C$_2$-C$_5$-alkenyl, -cyclopropylmethyl, or phenyl; and
R$^{8a}$ and R$^{8b}$ are each independently H, —C$_1$-C$_4$-alkyl, —NO$_2$, —NR$^4$R$^{23}$, —NR$^4$COOR$^{23}$, —Cl, —CH$_2$COOH, —S(O)$_x$-C$_1$-C$_4$-alkyl, NR$^4$CONR$^4$R$^{23}$, NR$^4$COR$^{23}$, CO$_2$R$^4$, —F, N[CH$_2$CH$_2$]$_2$NR$^{24}$, or N[CH$_2$CH$_2$]$_2$O.
R$^{23}$ is: methyl, ethyl, cyclopropyl, —CO cyclopropyl or 2-pyridyl.

4. The method of claim 3 wherein:
R$^1$ is
  (a) —CH$_2$SO$_2$NHCOR$^{23}$,
  (b) —1H-tetrazol-5-yl,
  (c) —SO$_2$NHCOR$^{23}$,
  (d) —SO$_2$NHCONR$^4$R$^{23}$,
  (e) —SO$_2$NHCOOR$^{23}$, or
  (f) —SO$_2$NHOR$^{23}$;
R$^6$ is -n-propyl, -ethyl, -iso-propyl, -n-butyl, -trans-2-butenyl, -cyclopropyl, or -cyclopropylmethyl;
R$^{8a}$ and R$^{8b}$ are each independently H, —NO$_2$, —C$_1$-C$_4$-alkyl, -NHCOCH$_3$, —S(O)$_x$—(C$_1$-C$_4$-alkyl), —N(CH$_3$)$_2$, —NHCOCH$_2$NH$_2$, —COOH, —COOCH$_3$, —CH$_2$OCOCH$_3$, —CH$_2$COOCH$_3$, —NHCON(R$^4$)$_2$, —NHCO$_2$R$^4$, —CH$_2$COOH, CH$_2$OH, or —NHMe, N[CH$_2$CH$_2$]$_2$NR$^{24}$, or N[CH$_2$CH$_2$]$_2$O.

5. The method of claim 2 wherein the compound is selected from the group consisting of:

[Structure diagram showing a biphenyl-substituted quinazolinone-like compound with labels R^8a, R^6, R^1]

| R$^1$ | R$^6$ | R$^{8a}$ |
|---|---|---|
| 1H-tetrazol-5-yl | cyclopropyl | N(pentyl)(benzoyl) |
| 1H-tetrazol-5-yl | cylcopropyl | N(benzyl)(benzoyl). |

6. The method of claim 1 wherein:

K is —C(O)—;

J and L are connected together to form a 6 carbon aromatic ring substituted with R$^{7a}$, R$^{7b}$, R$^{8a}$ and R$^{8b}$;

R$^1$ is
- (a) —NHSO$_2$R$^{23}$,
- (b) —NHSO$_2$NHCOR$^{23}$,
- (c) —NHCONHSO$_2$R$^{23}$,
- (d) —SO$_2$NHR$^{23}$,
- (e) —SO$_2$NHCOR$^{23}$,
- (f) —SO$_2$NHCONR$^4$R$^{23}$,
- (g) —SO$_2$NHCOOR$^{23}$,
- (h) —SO$_2$NHOR$^{23}$,
- (i) —CH$_2$SO$_2$NHCOR$^{23}$,
- (j) —CH$_2$SO$_2$NHCONHR$^{23}$,
- (k) —CO$_2$H, or
- (l) —1H-tetrazol-5-yl;

R$^{2a}$ is H;

R$^{2b}$ is H, F, Cl, CF$_3$, C$_1$-C$_4$-alkyl, C$_2$-C$_4$-alkenyl, or C$_2$-C$_4$-alkynyl, aryl or aryl-C$_1$-C$_6$-alkyl R$^{3a}$ is H;

R$^{3b}$ is H, F, Cl, CF$_3$, C$_1$-C$_4$-alkyl, C$_2$-C$_4$-alkenyl, C$_2$-C$_4$-alkynyl or C$_5$-C$_6$-cycloalkyl;

E is a single bond, —O— —S—, —SO$_2$—;

R$^6$ is
- (a) C$_1$-C$_5$-alkyl either in unsubstituted or substituted with a substituent selected from the group consisting of C$_3$-C$_5$-cycloalkyl, Cl, —O—CH$_3$, —OC$_2$H$_5$, or F,
- (b) C$_2$-C$_5$-alkenyl or C$_2$-C$_5$-alkynyl,
- (c) C$_3$-C$_5$-cycloalkyl, or
- (d) aryl;

R$^{7a}$ and R$^{7b}$ are independently
- (a) H;
- (b) C$_1$-C$_6$-alkyl, or
- (c) aryl;

R$^{8a}$ and R$^{8b}$ are independently
- (a) H,
- (b) C$_1$-C$_6$-alkyl or substituted C$_1$-C$_4$-alkyl with an COOR$^4$, OCOR$^{4a}$, OH, or aryl,
- (c) —OH,
- (d) —NO$_2$,
- (e) —NR$^4$COR$^{23}$,
- (f) —C$_1$-C$_4$-alkoxy,
- (g) —NR$^4$CO$_2$R$^{23}$,
- (h) —NR$^4$R$^{23}$,
- (i) —Cl, F, Br,
- (j) —CF$_3$,
- (k) —CO$_2$R$^4$,
- (l) —CO-aryl,
- (m) —S(O)$_x$—C$_1$-C$_4$-alkyl,
- (n) —SO$_2$—NH—C$_1$-C$_4$-alkyl,
- (o) —SO$_2$—NH-aryl,
- (p) —NR4SO$_2$CH$_3$,
- (q) —aryl,
- (r) —NR$^4$CONR$^4$R$^{23}$,
- (s) —N[CH$_2$CH$_2$]$_2$NR$^{24}$, or
- (t) —N[CH$_2$CH$_2$]$_2$O;

X is a single bond; and r is one.

7. The method of claim 6 wherein:

R$^1$ is:
- (a) —NHSO$_2$R$^{23}$,
- (b) —NHSO$_2$NHCOR$^{23}$,
- (c) —NHCONHSO$_2$R$^{23}$,
- (d) —SO$_2$NHR$^{23}$,
- (e) —SO$_2$NHCOR$^{23}$,
- (f) —SO$_2$NHCONR$^4$R$^{23}$,
- (g) —SO$_2$NHCOOR$^{23}$,
- (h) —SO$_2$NHOR$^{23}$,
- (i) —CH$_2$SO$_2$NHCOR$^{23}$,
- (j) —CH$_2$SO$_2$NHCONHR$^{23}$,
- (k) —1H-tetrazol-5-yl, or
- (l) —CO$_2$H;

E is a single bond;

r is one;

R$^6$ is —C$_1$-C$_4$-alkyl, -cyclopropyl, —CH$_2$CH$_2$CH$_2$CF$_3$, —CH$_2$CH$_2$CF$_3$, —C$_2$-C$_5$-alkenyl, -cyclopropylmethyl, or phenyl; and R$^{8a}$ and R$^{8b}$ are each independently H, —C$_1$-C$_4$-alkyl, —NO$_2$, —NR$^4$R$^{23}$, —NR$^4$COOR$^{23}$, —CH$_2$COOH, —S(O)$_x$—C$_1$-C$_4$-alkyl, —NR$^4$CONR$^4$R$^{23}$, —NR$^4$COR$^{23}$, —CO$_2$R$^4$, —F, —Cl, —Br, -aryl, —N[CH$_2$CH$_2$]$_2$NR$^{24}$ or —N[CH$_2$CH$_2$]$_2$O;

R$^{24}$ is: methyl, ethyl, cyclopropyl, —CO-cyclopropyl or 2-pyridyl.

8. The method of claim 7 wherein:

R$^1$ is
- (a) —CH$_2$SO$_2$NHCOR$^{23}$,
- (b) —1H-tetrazol-5-yl,
- (c) —SO$_2$NHCOR$^{23}$,
- (d) —SO$_2$NHCONR$^4$R$^{23}$,
- (e) —SO$_2$NHCOOR$^{23}$, or
- (f) —SO$_2$NHOR$^{23}$;

R$^6$ is -n-propyl, -ethyl, -iso-propyl, -n-butyl, -trans-2-butenyl, -cyclopropyl, or -cyclopropylmethyl;

R$^{8a}$ and R$^{8b}$ are each independently H, —NO$_2$, —C$_1$-C$_4$-alkyl, —NHCOCH$_3$, -aryl, —S(O)$_x$—(C$_1$-C$_4$-alkyl), —N(CH$_3$)$_2$, —NHCOCH$_2$NH$_2$, —COOH, —COOCH$_3$, —CH$_2$OCOCH$_3$, —CH$_2$COOCH$_3$, —NHCON(R$^4$)$_2$, —NHCO$_2$R$^4$, —CH$_2$COOH, CH$_2$OH, or —NHMe, —N[CH$_2$CH$_2$]$_2$NR$^{24}$, or N[CH$_2$CH$_2$]$_2$O.

9. The method of claim 6 which is a member of the group consisting of:

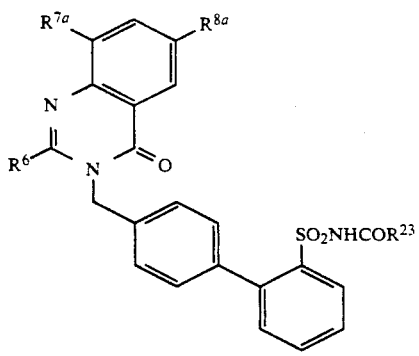

| R⁶ | R⁷ᵃ | R⁸ᵃ | R²³ |
|---|---|---|---|
| n-butyl | H | —N[CH₂CH₂]₂N-pyrid-2-yl | -cyclopropyl |
| isopropyl | CH₃ | —H | —CH₂CH₂CH(NHBoc)CO₂t-butyl |
| isopropyl | CH₃ | —H | —CH₂CH₂CH(NH₂)CO₂H |
| isopropyl | CH₃ | —H | —(CH₂)₅N(CH₃)₂ |
| butyl | H | —N[CH₂CH₂]₂NCOCH₃ | -cyclopropyl |
| propyl | H | —CH₃ | -cyclopropyl |
| butyl | CH₃ | —H | —(CH₂)₅NHBoc |
| butyl | CH₃ | —H | —(CH₂)₅NH₂ |
| butyl | H | -isopropyl | —CH₂CH₂-cyclopentyl |
| propyl | H | —N(CH₃)CO₂isobutyl | -phenyl |
| butyl | H | -isopropyl | —(CH₂)₅NHBoc |
| butyl | H | -isopropyl | —(CH₂)₅NH₂ |
| butyl | H | —N[CH₂CH₂]₂N-cyclopropyl | -cyclopropyl |
| propyl | H | -isopropyl | —(CH₂)₄CO₂CH₃ |
| propyl | H | —N(CH₃)CO₂-isobutyl | -cyclopropyl |
| ethyl | H | —N(benzyl)(benzoyl) | -phenyl |
| propyl | H | -isopropyl | —(CH₂)₄CO₂H |
| propyl | H | —N(pentyl)(benzoyl) | -cyclopropyl |
| propyl | H | —N(benzyl)CO₂-n-butyl | -cyclopropyl |
| propyl | H | —N(benzyl)CO₂-n-butyl | —CH₂NHBoc |
| propyl | H | —N(propyl)(acetyl) | -cyclopropyl |
| propyl | H | —N(pentyl)CO-cyclopropyl | -cyclopropyl |
| propyl | H | —N[CH₂CH₂]₂N-pyrid-2-yl | -cyclopropyl |
| propyl | H | -isopropyl | -cyclopropyl. |

10. The method of claim 6 which is a member of the group consisting of:

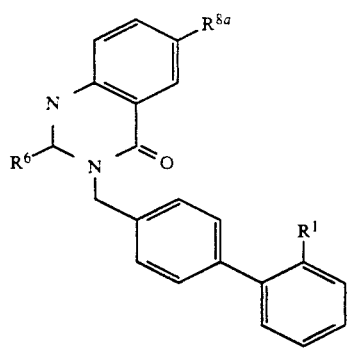

| R¹ | R⁶ | R⁸ᵃ |
|---|---|---|
| 1H-tetrazol-5-yl | n-propyl | —N(pentyl)(benzyl) |
| 1H-tetrazol-5-yl | methyl | —N(benzyl)CO₂-isobutyl |
| 1H-tetrazol-5-yl | n-butyl | —N(benzyl)CO₂-n-propyl |
| 1H-tetrazol-5-yl | n-propyl | —N(pentyl)CObenzyl |
| 1H-tetrazol-5-yl | n-propyl | —N(cyclohexyl)CO₂-n-propyl |
| 1H-tetrazol-5-yl | n-propyl | —N(benzyl)CO₂—CH₂CH₂OCH₃ |
| 1H-tetrazol-5-yl | n-propyl | —N(n-pentyl)(benzoyl) |
| 1H-tetrazol-5-yl | n-propyl | —N(benzyl)CO₂-t-butyl |
| 1H-tetrazol-5-yl | n-propyl | —N(benzyl)(SO₂-butyl) |
| 1H-tetrazol-5-yl | n-propyl | —N(n-pentyl)(4-chlorobenzoyl) |
| 1H-tetrazol-5-yl | n-propyl | —N(benzyl)CON(CH₃)(propyl) |
| 1H-tetrazol-5-yl | n-butyl | —N(benzyl)CON(CH₃)(propyl) |
| 1H-tetrazol-5-yl | n-propyl | —N(benzyl)CO₂isobutyl |
| 1H-tetrazol-5-yl | n-propyl | —N(4-methoxybenzyl)(5-methylpentanoyl) |

-continued

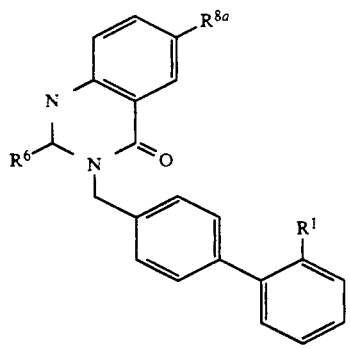

| R¹ | R⁶ | R⁸ᵃ |
|---|---|---|
| 1H-tetrazol-5-yl | n-propyl | —N(benzyl)CO₂CH₃ |
| 1H-tetrazol-5-yl | n-propyl | —N(benzyl)CO₂CH₂CH₃ |
| 1H-tetrazol-5-yl | n-propyl | —N(n-pentyl)CO-4-pyridyl |
| 1H-tetrazol-5-yl | n-propyl | —N(benzyl)(benzoyl) |
| 1H-tetrazol-5-yl | n-butyl | —SO₂N(benzyl)₂ |
| 1H-tetrazol-5-yl | n-propyl | —N(benzyl)CON(CH₃)(CH₂CH₃) |
| 1H-tetrazol-5-yl | n-propyl | —N(n-pentyl)CO-2-furanyl |
| 1H-tetrazol-5-yl | n-propyl | —N(4-benzyloxybenzyl)(2-methylpentanoyl) |
| 1H-tetrazol-5-yl | n-propyl | —N(4-hydroxybenzyl)(2-methylpentanoyl) |
| 1H-tetrazol-5-yl | ethyl | —N(4-fluorobenzyl)(benzoyl) |
| 1H-tetrazol-5-yl | ethyl | —N(n-pentyl)SO₂-butyl |
| 1H-tetrazol-5-yl | n-propyl | —N(CH₃)CO₂-isobutyl |
| 1H-tetrazol-5-yl | n-propyl | —N(benzyl)CO₂-isobutyl |
| 1H-tetrazol-5-yl | ethyl | —N(benzyl)CONH-propyl |
| 1H-tetrazol-5-yl | cyclopropyl | —N(n-pentyl)benzoyl |
| 1H-tetrazol-5-yl | cyclopropyl | —N(benzyl)benzoyl |
| 1H-tetrazol-5-yl | propyl | —N(butyl)CO-4-pyridyl |
| 1H-tetrazol-5-yl | methyl | —N(benzyl)benzoyl |
| 1H-tetrazol-5-yl | ethyl | —N(benzyl)SO₂-propyl |
| 1H-tetrazol-5-yl | isopropyl | —N(benzyl)benzoyl |
| 1H-tetrazol-5-yl | propyl | —N(n-pentyl)CO-4-pyridyl |
| 1H-tetrazol-5-yl | ethyl | —N(benzyl)CO-4-pyridyl |
| 1H-tetrazol-5-yl | propyl | —N(n-pentyl)(4-thiomethylbenzoyl) |
| 1H-tetrazol-5-yl | ethyl | —N(benzyl)(2-chlorobenzoyl) |
| 1H-tetrazol-5-yl | ethyl | —N(2-chlorobenzyl)(2-chlorobenzoyl) |
| 1H-tetrazol-5-yl | ethyl | —N(n-pentyl)(4-sulfonylmethylbenzoyl) |
| 1H-tetrazol-5-yl | propyl | —N(n-pentyl)(4-sulfonylmethylbenzoyl) |
| 1H-tetrazol-5-yl | propyl | —N(CH₂CH₂CHO)(benzyoyl) |
| 1H-tetrazol-5-yl | ethyl | —N(2-chlorobenzyl)(benzoyl) |
| 1H-tetrazol-5-yl | propyl | —N(propyl)(4-fluorobenzoyl) |
| 1H-tetrazol-5-yl | ethyl | —N(4-methylbutyl)(benzoyl) |
| 1H-tetrazol-5-yl | isopropyl | —N(2-chlorobenzyl(benzoyl) |
| 1H-tetrazol-5-yl | H | —N(benzyl)(benzoyl) |
| 1H-tetrazol-5-yl | H | —N(2-chlorobenzyl)(benzoyl) |
| 1H-tetrazol-5-yl | ethyl | —N(4-chlorobenzyl)(benzoyl) |
| 1H-tetrazol-5-yl | ethyl | —N(2-fluorobenzyl)(benzoyl) |
| 1H-tetrazol-5-yl | ethyl | —N(3-chlorobenzyl)(benzoyl) |
| 1H-tetrazol-5-yl | isobutyl | —N(benzyl)(benzoyl) |
| 1H-tetrazol-5-yl | isobutyl | —N(2-chlorbenzyl)(benzoyl) |
| 1H-tetrazol-5-yl | methyl | —N(2-chlorbenzyl)(benzoyl) |
| 1H-tetrazol-5-yl | methyl | -(benzyl)CO-4-pyridyl |
| 1H-tetrazol-5-yl | methyl | —N(4-methylbut-2-enyl)CO-4-pyridyl) |
| 1H-tetrazol-5-yl | propyl | —N(CH₂-4-pyridyl)CO₂-n-propyl |
| 1H-tetrazol-5-yl | propyl | —N(n-pentyl)CO-2-thienyl |
| 1H-tetrazol-5-yl | ethyl | —N(benzyl)(4-iodobenzoyl) |
| 1H-tetrazol-5-yl | ethyl | —N(2-iodobenzyl)(benzoyl) |
| 1H-tetrazol-5-yl | ethyl | —N(benzyl)CO-2-thienyl |
| 1H-tetrazol-5-yl | propyl | —N(4-fluorobenzyl)CON(CH₃)(isopropyl). |

11. The method of claim 1 wherein:
K is —C(=NR²²)—;
J and L are connected together to form a 6 carbon aromatic ring substituted with R⁷ᵃ, R⁷ᵇ, R⁸ᵃ and R⁸ᵇ;
R¹ is
(a) —NHSO₂R²³,
(b) —NHSO₂NHCOR²³,
(c) —NHCONHSO₂R²³,
(d) —SO₂NHR²³,
(e) —SO₂NHCOR²³,
(f) —SO₂NHCONR⁴R²³,
(g) —SO₂NHCOOR²³,
(h) —SO₂NHOR²³,
(i) —CH₂SO₂NHCOR²³,
(j) —CH₂SO₂NHCONHR²³,
(k) —CO₂H, or
(l) —1H-tetrazol-5-yl;
R²ᵃ is H;
R²ᵇ is H, F, Cl, CF₃, C₁–C₆-alkyl, C₂–C₄-alkenyl or C₂–C₄-alkynyl;
R³ᵃ is H;

$R^{3b}$ is H, F, Cl, $CF_3$, $C_1$-$C_4$-alkyl, $C_2$-$C_4$-alkenyl, $C_2$-$C_4$-alkynyl or $C_5$-$C_6$-cycloalkyl;

E is a single bond, —O— —S—, —$SO_2$—;

$R_6$ is
- (a) $C_1$-$C_5$-alkyl either substituted or unsubstituted $C_1$-$C_5$-alkyl with a substituent selected from the group consisting of $C_3$-$C_5$-cycloalkyl, Cl, —O—$CH_3$, —$OC_2H_5$, or F,
- (b) $C_2$-$C_5$-alkenyl or $C_2$-$C_5$-alkynyl,
- (c) $C_3$-$C_5$-cycloalkyl, or
- (d) aryl;

$R^{7a}$ and $R^{7b}$ are independently
- (a) H;
- (b) $C_1$-$C_6$-alkyl, or
- (c) aryl;

$R^{8a}$ and $R^{8b}$ are independently
- (a) H,
- (b) $C_1$-$C_4$-alkyl or substituted $C_1$-$C_4$-alkyl with an $COOR^4$, $OCOR^{4a}$, OH, or aryl,
- (c) —OH,
- (d) —$NO_2$,
- (e) —$NR^4COR^{23}$,
- (f) —$C_1$-$C_4$-alkoxy,
- (g) —$NR^4CO_2R^{23}$,
- (h) —$NR^4R^{23}$,
- (i) —Cl, F, Br,
- (j) —$CF_3$,
- (k) —$CO_2R^4$,
- (l) —CO—aryl,
- (m) —$S(O)_x$—$C_1$-$C_4$-alkyl,
- (n) —$SO_2$—NH—$C_1$-$C_4$-alkyl,
- (o) —$SO_2$—NH-aryl,
- (p) —$NR4SO_2CH_3$,
- (q) —aryl,
- (r) —$NR^4CONR^4R^{23}$,
- (s) —$N[CH_2CH_2]_2NR^{24}$, or
- (t) —$N[CH_2CH_2]_2O$;

X is a single bond and;

r is one.

12. The method of claim 11 wherein:
$R^1$ is:
- (a) —$NHSO_2R^{23}$,
- (b) —$NHSO_2NHCOR^{23}$,
- (c) —$NHCONHSO_2R^{23}$,
- (d) —$SO_2NHR^{23}$,
- (e) —$SO_2NHCOR^{23}$,
- (f) —$SO_2NHCONR^4R^{23}$,
- (g) —$SO_2NHCOOR^{23}$,
- (h) —$SO_2NHOR^{23}$,
- (i) —$CH_2SO_2NHCORR^{23}$,
- (j) —$CH_2SO_2NHCONHR^{23}$, or
- (k) —1H-tetrazol-5-yl;

E is a single bond;

r is one;

$R^6$ is —$C_1$-$C_4$-alkyl, -cyclopropyl, —$CH_2CH_2CH_2CF_3$, —$CH_2CH_2CF_3$, —$C_2$-$C_5$-alkenyl, -cyclopropylmethyl, or phenyl; and $R^{8a}$ and $R^{8b}$ are each independently H, —$C_1$-$C_4$-alkyl, —$NO_2$, —$NR^4R^{23}$, —$NR^4COOR^{23}$, —Cl, —$CH_2COOH$, —$S(O)_x$—$C_1$-$C_4$-alkyl, -aryl, $NR^4CONR^4R^{23}$, $NR^4COR^{23}$, $CO_2R^4$, —F —Cl, —Br, —$N[CH_2CH_2]_2NR^{24}$, or —$N[CH_2CH_2]_2O$.

13. The method of claim 12 wherein:
$R^1$ is
- (a) —$CH_2SO_2NHCOR^{23}$,
- (b) —1H-tetrazol-5-yl,
- (c) —$SO_2NHCOR^{23}$,
- (d) —$SO_2NHCONR^4R^{23}$,
- (e) —$SO_2NHCOOR^{23}$, or
- (f) —$SO_2NHOR^{23}$;

$R^6$ is -n-propyl, iso-propyl ethyl, -n-butyl, -trans-2-butenyl, -cyclopropyl, or -cyclopropylmethyl;

$R^{8a}$ and $R^{8b}$ are each independently H, —$NO_2$, —$C_1$-$C_4$-alkyl, —$NHCOCH_3$, -aryl, —$S(O)_x$—($C_1$-$C_4$-alkyl), —$N(CH_3)_2$, —$NHCOCH_2NH_2$, —COOH, —$COOCH_3$, —$CH_2OCOCH_3$, —$CH_2COOCH_3$, —$NHCON(R^4)_2$. —$NHCO_2R^4$, —$CH_2COOH$, $CH_2OH$, —NHMe, —$N[CH_2CH_2]_2NR^{24}$, or —$N[CH_2CH_2]_2O$.

14. The method of claim 1 wherein the central nervous system disorder is selected from the group consisting of psychoses, depression, cognitive dysfunction, anxiety, tardive dykinesia, drug dependency, panic attack and mania.

* * * * *